(12) United States Patent
Konishi et al.

(10) Patent No.: US 11,426,127 B2
(45) Date of Patent: Aug. 30, 2022

(54) HOLDING INSTRUMENT, MEASUREMENT APPARATUS AND MEASUREMENT METHOD

(71) Applicant: KYOCERA Corporation, Kyoto (JP)

(72) Inventors: Tomoaki Konishi, Yokohama (JP); Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 155 days.

(21) Appl. No.: 16/604,997

(22) PCT Filed: Apr. 5, 2018

(86) PCT No.: PCT/JP2018/014568
§ 371 (c)(1),
(2) Date: Oct. 12, 2019

(87) PCT Pub. No.: WO2018/198708
PCT Pub. Date: Nov. 1, 2018

(65) Prior Publication Data
US 2020/0155076 A1 May 21, 2020

(30) Foreign Application Priority Data
Apr. 26, 2017 (JP) .............................. JP2017-087715

(51) Int. Cl.
*A61B 5/00* (2006.01)
*A61B 5/11* (2006.01)
(Continued)

(52) U.S. Cl.
CPC .......... *A61B 5/6896* (2013.01); *A61B 5/1102* (2013.01); *A61B 5/113* (2013.01);
(Continued)

(58) Field of Classification Search
CPC ... A61B 5/6896; A61B 5/1102; A61B 5/1126; A61B 5/113; A61B 5/7405; A61B 5/742;
(Continued)

(56) References Cited

U.S. PATENT DOCUMENTS 6,397,398 B1 * 6/2002 Herder .................... A41D 27/20
2/249
8,458,830 B1 * 6/2013 Pierce .................... A41B 13/06
5/413 R
(Continued)

FOREIGN PATENT DOCUMENTS

CN        105900410 A  *  8/2016  .............. G21F 3/02
JP        2002-360530 A    12/2002
(Continued)

*Primary Examiner* — Sean P Dougherty
*Assistant Examiner* — Jonathan E. Cooper
(74) *Attorney, Agent, or Firm* — Studebaker & Brackett PC

(57) ABSTRACT

A holding instrument includes a holding portion that holds a measurement apparatus. The measurement apparatus includes a gyro sensor that detects change in a measured part of a user and a controller that performs a process of measuring biological information of the user based on output of the gyro sensor. The holding instrument is embraced by the user during use while the holding portion is holding the measurement apparatus.

16 Claims, 22 Drawing Sheets

(51) Int. Cl.
*A61B 5/113* (2006.01)
*A61B 5/024* (2006.01)

(52) U.S. Cl.
CPC ............ *A61B 5/1126* (2013.01); *A61B 5/742* (2013.01); *A61B 5/7405* (2013.01); *A61B 5/7455* (2013.01); *A61B 5/02438* (2013.01); *A61B 5/6802* (2013.01); *A61B 5/6843* (2013.01); *A61B 2562/0219* (2013.01)

(58) Field of Classification Search
CPC . A61B 5/7455; A61B 2562/0219; A61B 5/11; A61B 5/6835; A61B 5/683; A61B 5/6879; A61B 5/6885; A61B 5/6882; A61B 5/6801; A61B 5/0816; A61B 5/6802; A61B 5/02438; A61B 5/6843; A47C 21/026; A47G 9/0253; A63H 3/02
See application file for complete search history.

(56) References Cited

U.S. PATENT DOCUMENTS

| | | | |
|---|---|---|---|
| 8,795,205 B2* | 8/2014 | Maity | A61B 5/103 600/591 |
| 9,491,508 B2* | 11/2016 | Nielsen | H04N 21/44218 |
| 10,390,761 B2 | 8/2019 | Ajima | |
| 2002/0188210 A1 | 12/2002 | Aizawa | |
| 2004/0073123 A1* | 4/2004 | Hessel | A61B 5/681 600/490 |
| 2005/0066443 A1* | 3/2005 | Rivera-Wienhold | A47D 13/08 5/632 |
| 2011/0267196 A1 | 11/2011 | Hu et al. | |
| 2014/0231277 A1* | 8/2014 | Ponski | A45F 5/02 206/38 |
| 2016/0058385 A1* | 3/2016 | Ajima | A61B 5/02007 600/485 |
| 2016/0074760 A1* | 3/2016 | Parker | A63H 3/02 446/72 |
| 2016/0174901 A1* | 6/2016 | Majic | A61B 5/02055 600/301 |
| 2017/0164663 A1* | 6/2017 | Korenek | B60N 2/80 |
| 2018/0000356 A1* | 1/2018 | Ajima | A61B 5/7275 |

FOREIGN PATENT DOCUMENTS

JP  2005-040440 A  2/2005
WO  2014/171465 A1  10/2014

* cited by examiner

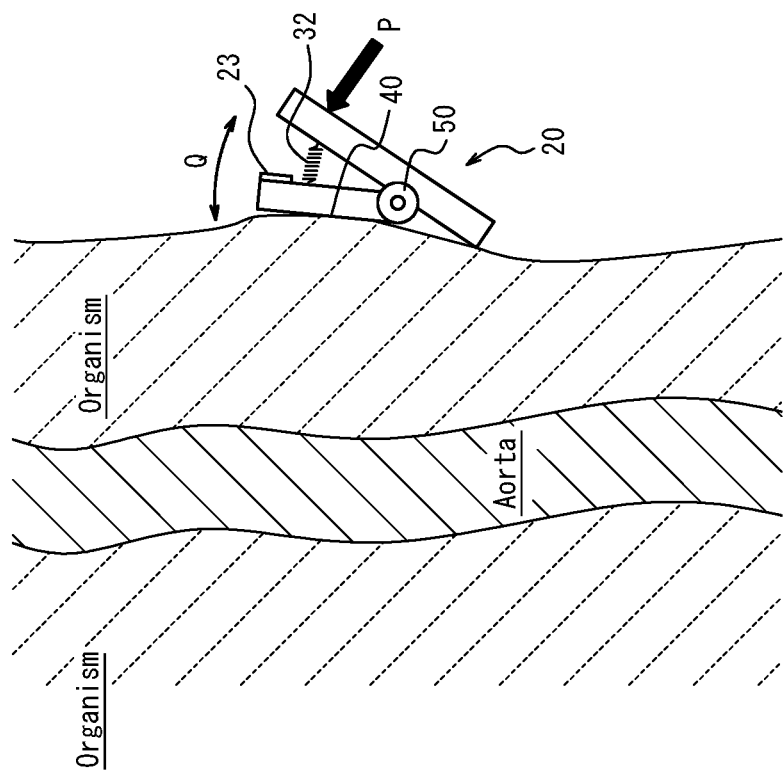
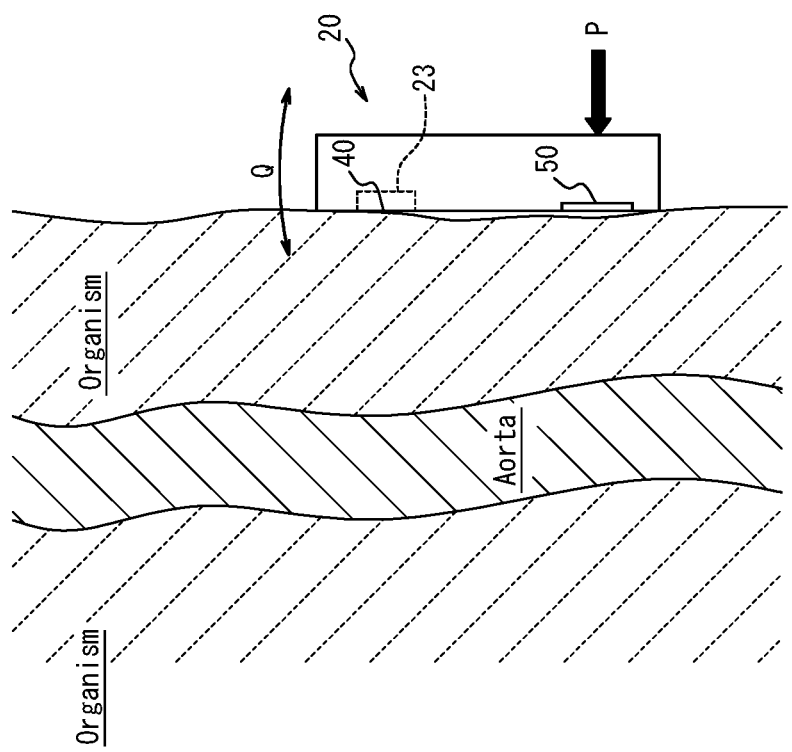

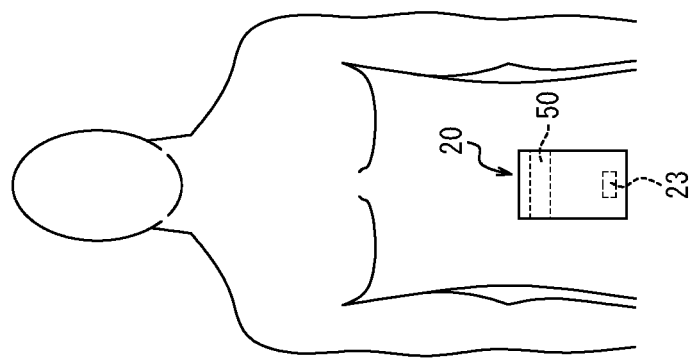
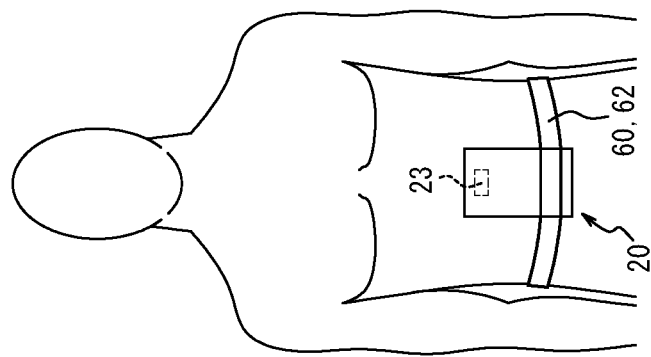
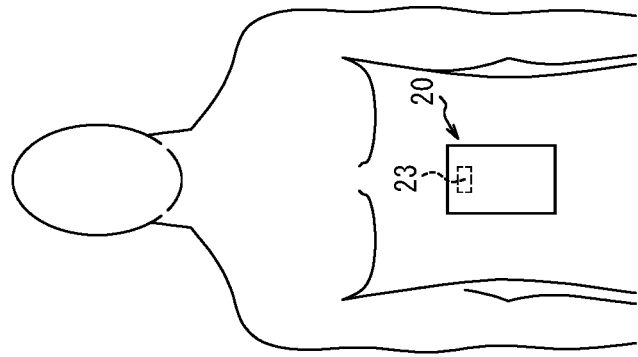

Current cycle

Target cycle

HOLDING INSTRUMENT, MEASUREMENT APPARATUS AND MEASUREMENT METHOD

CROSS-REFERENCE TO RELATED APPLICATION

The present application claims priority to and the benefit of Japanese Patent Application No. 2017-087715 filed Apr. 26, 2017, the entire contents of which are incorporated herein by reference.

TECHNICAL FIELD

The present disclosure relates to a holding instrument, a measurement apparatus, and a measurement method.

BACKGROUND

An electronic device that measures biological information at the wrist or other measured part of a user is known. For example, the electronic device measures a user's pulse beat while attached to the user's wrist.

SUMMARY

A holding instrument according to an aspect includes a holding portion configured to hold a measurement apparatus. The measurement apparatus includes a gyro sensor configured to detect change in a measured part of a user and a controller configured to perform a process of measuring biological information of the user based on output of the gyro sensor. The holding instrument is embraced by the user during use while the holding portion is holding the measurement apparatus.

A measurement apparatus according to an aspect includes a housing, a gyro sensor disposed in the housing and configured to detect change in a measured part of a user, and a controller configured to perform a process of measuring biological information of the user based on output of the gyro sensor. The measurement apparatus is embraced by the user during use.

A measurement method according to an aspect is for a measurement apparatus including a gyro sensor configured to detect change in a measured part of a user. The measurement method includes performing a process of measuring biological information of the user based on output of the gyro sensor while the user is embracing a holding instrument that holds the measurement apparatus.

BRIEF DESCRIPTION OF THE DRAWINGS

In the accompanying drawings:

FIGS. 5A and 5B illustrate examples of the abutment state between the measured part and the abutting portion;

FIGS. 6A, 6B, and 6C illustrate forms of abutment of the measurement apparatus against the torso of a user;

DETAILED DESCRIPTION

Embodiments are described below in detail with reference to the drawings.

Figure 1A:
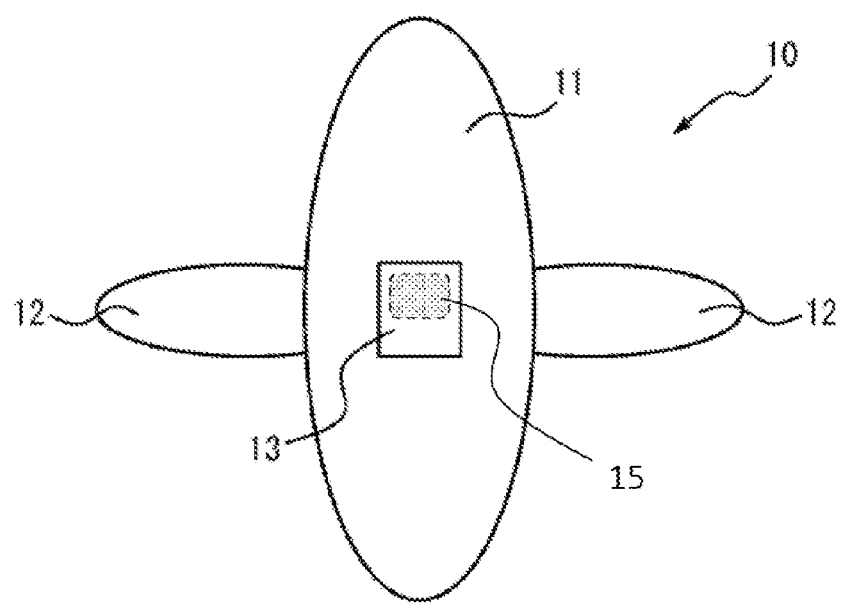
FIGS. 1A and 1B are conceptual diagrams illustrating the appearance of a holding instrument according to an embodiment.
Figure 1B:
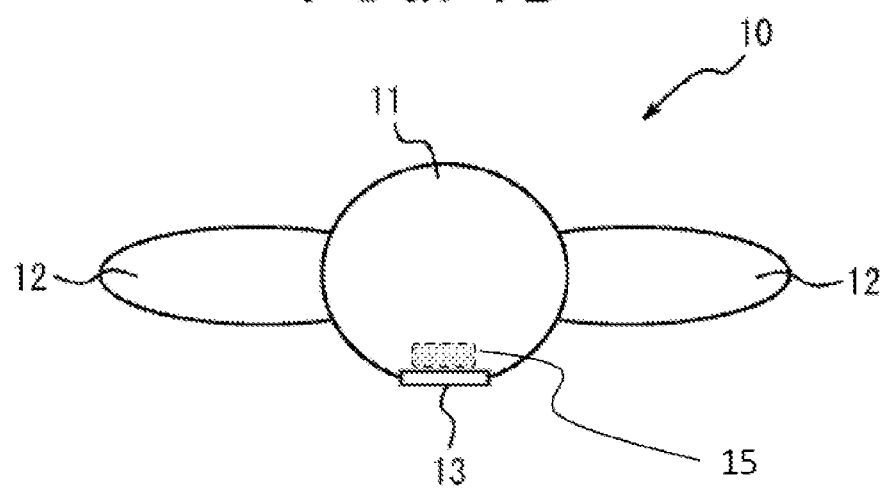

FIGS. 1A and 1B are conceptual diagrams illustrating the appearance of a holding instrument 10 according to an embodiment. FIG. 1A is a front view of the holding instrument 10, and FIG. 1B is a top view. The holding instrument 10 according to the present embodiment includes a main body 11, an arm 12, and a holding portion 13. The holding instrument 10 is embraced by the user during use. The holding instrument 10 may, for example, be configured overall as a body pillow. In the present embodiment, the holding instrument 10 is described as being a body pillow. The holding instrument 10 is used while holding a measurement apparatus, described below, in the holding portion 13. The measurement apparatus held in the holding portion 13 measures biological information while the holding instrument 10 is embraced.

The main body 11 is embraced by the user while the holding instrument 10 is used. The main body 11 of the holding instrument 10 in FIGS. 1A and 1B is an ellipsoid that is elongated in the height direction in a front view. The shape of the main body 11 is not, however, limited to an ellipsoid. The main body 11 may have any shape that can be embraced by the user, such as a substantially cylindrical shape. The main body 11 may be configured to include cushioning material. For example, the main body 11 may include cotton, buckwheat husks, sponge, or kapok on the inside. The user can embrace the holding instrument 10 more easily when the main body 11 is cushioned.

The arm 12 is a member joined to the main body 11. The main body 11 may include a plurality of arms 12. In the present embodiment, the main body 11 includes two arms 12 that are symmetrical in front view. The arms 12 may be deformable. For example, the arms 12 may be bendable into a shape that hugs the user while the user is embracing the holding instrument 10. The arms 12 may also be cushioned like the main body 11.

The holding portion 13 holds the measurement apparatus, described below. In other words, the holding portion 13 can hold the measurement apparatus on the inside. In the example in FIGS. 1A and 1B, the holding portion 13 is attached to the front side of the main body 11. The holding portion 13 is provided at a position that contacts the measured part when the measurement apparatus is held inside the holding portion 13 and the holding instrument 10 is held by the user. The measured part is a part at which the measurement apparatus measures the user's biological information. In the present embodiment, the measured part is described as being the user's torso.

The holding portion 13 may, for example, be configured as a bag-shaped cloth pocket sewn onto the front of the main body 11. The holding portion 13 may, for example, include a mechanism capable of sustaining a holding state such that the measurement apparatus held on the inside does not fall out from the holding portion 13. For example, the holding portion 13 may include a surface fastener, a wire fastener, or the like. After inserting the measurement apparatus in the holding portion 13, the user can close the surface fastener or wire fastener to prevent the measurement apparatus from falling out from the holding portion 13. The holding portion 13 may include a mechanism for securing the measurement apparatus on the inside.

The state of attachment of the holding portion 13 to the main body 11 of the holding instrument 10 may be adjustable. The state of attachment may, for example, include at least one of an attachment angle and an attachment position.

For example, the holding portion 13 may be attached to the main body 11 via a ratchet 15 capable of adjusting the angle relative to the main body 11. By adjusting the angle of the holding portion 13 relative to the main body 11, the user can adjust the abutment state of the measurement apparatus, which is held inside the holding portion 13, against the measured part when the user embraces the holding instrument 10.

The holding portion 13 may, for example, be configured to be capable of changing the attachment position relative to the main body 11. For example, the holding portion 13 may be configured as a member that is independent from the main body 11 and is capable of attaching to predetermined positions of the main body 11 during use. A change in the attachment position of the holding portion 13 relative to the main body 11 changes the position at which the measurement apparatus held inside the holding portion 13 abuts against the user when the user embraces the holding instrument 10. The measured part can thus be changed without a change in the way the holding instrument 10 is embraced.

The holding portion 13 may be configured so that a notification outputted by the measurement apparatus is recognizable by the user. While details are provided below, the notification may, for example, include at least one of sound, screen display, and vibration. In other words, the holding portion 13 may be configured as a member, and/or in a form, that allows the user to recognize sound, screen display, and vibration. For example, when the holding portion 13 is configured as a member that is transparent on the front side, the user can recognize the screen display by the measurement apparatus.

The holding instrument 10 may include a plurality of holding portions 13 at different positions. When the holding instrument 10 includes a plurality of holding portions 13, the user can change the position at which the measurement apparatus abuts against the user by inserting the measurement apparatus in a different holding portion 13.

The holding instrument 10 may be configured overall to be adaptable to the user's body. Adaptable to the user's body refers to the holding instrument 10 being easy for the user to embrace, or support being provided to maintain the state in which the user is embracing the holding instrument 10. For example, the holding instrument 10 may include linear grooves on the main body 11 at the positions where the user embraces the holding instrument 10. In this case, the user can embrace the main body 11 by placing the arms in the linear grooves provided in the main body 11, making the holding instrument 10 easier to embrace. Furthermore, the embracement is easier to maintain when the arms are placed in the groove.

For example, the holding instrument 10 may have a concave shape, at the front of the main body 11, corresponding to the shape of the front (abdominal) side of a human body. The user can embrace the holding instrument 10 by fitting the abdomen to the concave portion. This makes it easier for the user to embrace the holding instrument 10.

For example, the arms 12 of the holding instrument 10 may be curved to support maintaining embracement of the holding instrument 10.

Besides the above examples, the holding instrument 10 may have any shape conforming to a torso or other human shape.

The holding instrument 10 may be shaped in accordance with the user's body shape. For example, the holding instrument 10 may be configured to have a shape easy for the user to embrace in accordance with the user's body shape, such as the user's height, shoulder width, abdominal girth, arm or leg length, or other traits. It is easier for each user to embrace the holding instrument 10 when the holding instrument 10 has a shape corresponding to the user's body shape.

Next, the measurement apparatus held in the holding portion 13 is described in detail.

The measurement apparatus is assumed to be a mobile phone, such as a smartphone, in the present disclosure. The measurement apparatus is not, however, limited to the example of a smartphone and may be a mobile phone such as a feature phone, for example. The measurement apparatus is not necessarily limited to a mobile phone, either, and can be a variety of mobile communication terminals such as a tablet, a remote control for operating an electronic device, a digital camera, or a laptop PC. The measurement apparatus may be a dedicated apparatus having a function to measure the biological information described below. In sum, the measurement apparatus can be any apparatus having a function to measure biological information.

Figure 2:
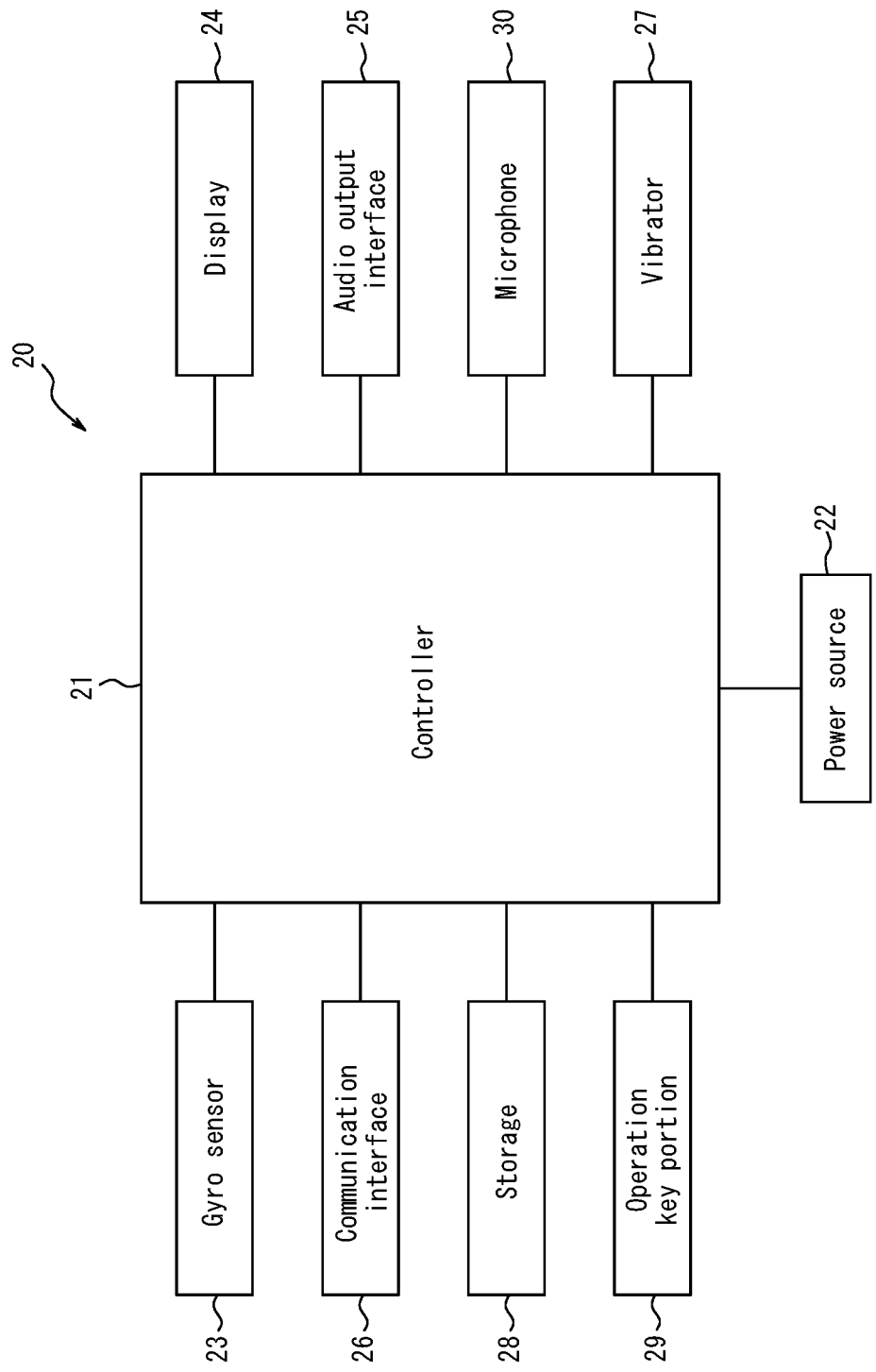
FIG. 2 is a functional block diagram illustrating an example schematic configuration of a measurement apparatus.

FIG. 2 is a functional block diagram schematically illustrating an example of the configuration of a measurement apparatus 20. As illustrated in FIG. 2, the measurement apparatus 20 includes a controller 21, a power source 22, a gyro sensor 23, a display 24, an audio output interface 25, a communication interface 26, a vibrator 27, a storage 28, an operation key portion 29, and a microphone 30.

The controller 21 includes a processor for overall control and management of the measurement apparatus 20, including the functional blocks of the measurement apparatus 20. The controller 21 includes a processor, such as a central processing unit (CPU), that executes a program with prescribed control procedures and a program for measuring biological information of the user. Such programs may, for example, be stored in the storage 28 or on an external storage medium or the like connected to the measurement apparatus 20.

The controller 21 may perform control to implement the functions of the measurement apparatus 20. For example, when the measurement apparatus 20 is a smartphone, the controller 21 may perform control to implement a function related to phone calls or data communication and a function related to execution of application programs.

The power source 22 includes a battery and provides a source of power to each component of the measurement apparatus 20. During operation, the measurement apparatus 20 receives a supply of power from the power source 22 or an external power source.

The gyro sensor 23 detects displacement of the measurement apparatus 20 as a motion factor by detecting the angular velocity of the measurement apparatus 20. The gyro sensor 23 may, for example, be a three-axis vibration gyro sensor that detects the angular velocity from deformation of a structure due to the Coriolis force acting on a vibrated arm. The material for this structure may, for example, be made of crystal or a piezoelectric material such as piezoelectric ceramic. The gyro sensor 23 may also be formed by micro-electro-mechanical systems technology using silicon material or the like for the structure. The gyro sensor 23 may adopt a different system, such as an optical gyro sensor. The controller 21 can measure the orientation of the measurement apparatus 20 by integrating the angular velocity, acquired by the gyro sensor 23, over time once.

The gyro sensor 23 is, for example, an angular velocity sensor. The gyro sensor 23 is not, however, limited to an angular velocity sensor. The gyro sensor 23 may detect the angular displacement of the measurement apparatus 20 as a motion factor. The gyro sensor 23 detects a motion factor processed as a self-control factor. The motion factor detected by the gyro sensor 23 is transmitted to the controller 21.

The controller 21 acquires the motion factor from the gyro sensor 23.

The motion factor includes an index indicating displacement of the measurement apparatus 20 based on pulsation at the measured part of the user. The controller 21 generates the user's pulsation based on the motion factor. The controller 21 measures biological information based on the user's pulsation. Details of the process by which the controller 21 measures biological information are provided below.

The display 24 includes a display device such as a liquid crystal display, an organic Electro-Luminescence (EL) panel, or an inorganic EL panel. The display 14 displays characters, images, symbols, graphics, or the like. The display 14 may be configured as a touchscreen display that includes not only a display function but also the function of a touchscreen. In this case, the touchscreen detects contact by the user's finger, a stylus pen, or the like. The touchscreen can detect the position on the touchscreen contacted by a plurality of fingers, stylus pens, or the like. Any detection system may be used in the touchscreen, such as a capacitive system, a resistive film system, a surface acoustic wave system (or an ultrasonic wave system), an infrared system, an electromagnetic induction system, or a load detection system. When the touchscreen uses a capacitive system, contact and proximity of a finger, stylus pen, or the like can be detected.

The audio output interface 25 notifies the user or the like of information by outputting sound. The audio output interface 25 can be configured by any appropriate speaker or the like. The audio output interface 25 outputs sound signals, transmitted from the controller 21, as sound. During a phone call using the measurement apparatus 20, for example, the user can hear the other party's voice from the audio output interface 25. In this case, the user can place an ear against the audio output interface 25 to hear the other party's voice outputted from the audio output interface 25. When the audio output interface 25 is used as a speakerphone, for example, the user can hear the other party's voice without placing an ear against the audio output interface 25.

The communication interface 26 exchanges a variety of data with an external apparatus by wired or wireless communication. The communication interface 26 can connect to and communicate with the base station or the like to implement the functions of phone calling and/or data communication by the measurement apparatus 20. The communication interface 26 can, for example, transmit the measurement results of biological information measured by the measurement apparatus 20 to an external apparatus. The communication interface 26 can communicate with an external apparatus that stores the user's biological information, in which case the state of health can be managed on the external apparatus.

The vibrator 27 notifies the user or the like of information by generating vibration. The vibrator 27 presents a tactile sensation to the user of the measurement apparatus 20 by generating vibration at any part of the measurement apparatus 20. The vibrator 27 may be configured to include any material that generates vibration. The vibrator 27 may be configured to include an eccentric motor, a piezoelectric element, a linear vibrator, or the like.

The storage 28 stores various programs, starting with application programs, and data. The storage 28 may include any non-transitory storage medium, such as a semiconductor storage medium or a magnetic storage medium. The storage 28 may also include a plurality of types of storage media. The storage 28 may include a combination of a portable storage medium, such as a memory card, optical disc, or magneto-optical disc, and an apparatus for reading the storage medium. The storage 28 may include a storage device used as a volatile storage area, such as random access memory (RAM). The storage 28 stores a variety of information, programs for causing the measurement apparatus 20 to operate, and the like and also functions as a working memory. The storage 28 may, for example, store data detected by the gyro sensor 23, the result of measuring biological information, and the like.

The operation key portion 29 is configured by one or more operation keys that detect user operation input. The operation key portion 29 can be configured as any type of key, button, or the like, such as a push-button switch or a slide switch. When the measurement apparatus 20 is configured so that all operations can be performed on a touchscreen display, the operation key portion 29 may be omitted.

The microphone 30 converts detected sound to an audio signal. The microphone 30 may be configured in any way capable of detecting sound. The microphone 30 transmits the converted audio signal to the controller 21. The controller 21 can, for example, transmit the received audio signal via the communication interface 26. Consequently, the measurement apparatus 20 can transmit audio inputted to the microphone 30 to the other party during a telephone call that the user makes with the measurement apparatus 20.

The measurement apparatus 20 is not limited to the configuration in FIG. 2. The essential components for the measurement apparatus 20 to measure the biological information are the controller 21 and the gyro sensor 23. As necessary, components other than these essential components may therefore be omitted from the measurement apparatus 20, or other components may be added. The gyro sensor 23, which is an essential component for the measurement apparatus 20 to measure the biological information, is not necessarily built into the measurement apparatus 20. In this case, the gyro sensor 23 may be included in an external member, such as a case or an attachment that can be mounted on the measurement apparatus 20.

The measurement apparatus 20 can measure biological information at the measured part of the user. The measured part may, for example, be the user's torso, as described below. The measurement apparatus 20 measures biological information of the user based on change in the torso, which is the measured part.

The biological information measured by the measurement apparatus 20 may, for example, include at least one of blood components, pulse waves, pulse beats, and pulse wave propagation rate. The blood components include the state of glucose metabolism and the state of lipid metabolism, for example. The state of glucose metabolism includes the blood glucose level, for example. The state of lipid metabolism includes the lipid level, for example. The lipid level includes neutral lipids, total cholesterol, high-density lipoprotein (HDL) cholesterol, low-density lipoprotein (LDL) cholesterol, and the like. The measurement apparatus 20 may, for example, acquire the user's pulse wave as the biological information and may measure biological information such blood components based on the acquired pulse wave.

Figure 3A:
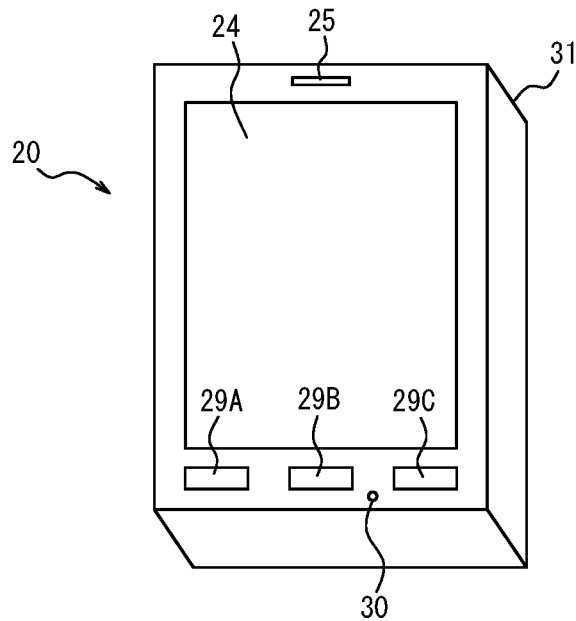
FIGS. 3A and 3B are schematic perspective views illustrating an example of the appearance of the measurement apparatus.
Figure 3B:
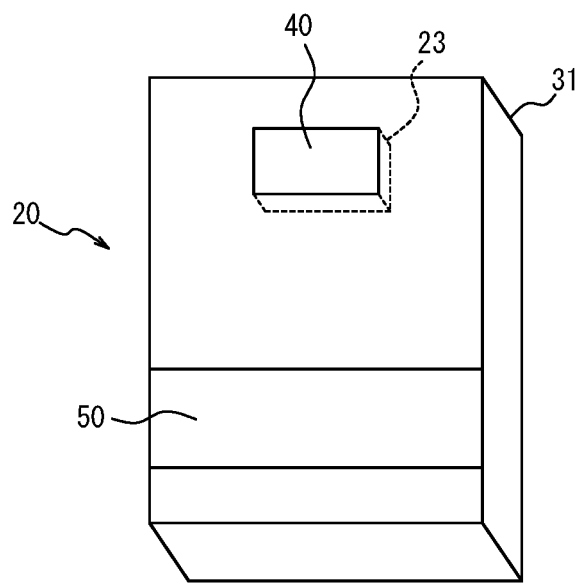

FIGS. 3A and 3B are schematic perspective views illustrating an example of the appearance of the measurement apparatus 20. As illustrated in FIGS. 3A and 3B, for example, the measurement apparatus 20 can be configured as a mobile communication terminal such as a relatively small mobile phone. However, the measurement apparatus 20 is not limited to a mobile communication terminal such as a mobile phone. The measurement apparatus 20 may, for example, be incorporated into any portable electronic device.

FIG. 3A illustrates the front of the measurement apparatus 20. FIG. 3B illustrates the back of the measurement apparatus 20, i.e. the measurement apparatus 20 in FIG. 3A when flipped over.

As illustrated in FIGS. 3A and 3B, the measurement apparatus 20 includes a housing 31 with a substantially rectangular appearance. The measurement apparatus 20 includes the display 24, the audio output interface 25, the operation key portion 29, and the microphone 30 on the front side, as illustrated in FIG. 3A. The display 24 can display information related to the measurement process by the measurement apparatus 20. By looking at the display on the display 24, the user can confirm the measurement status while measuring the biological information. The user can also confirm the result of measuring biological information by looking at the display on the display 24. Furthermore, the user can look at the display on the display 14 to confirm whether the biological information is being measured properly. The display 24 may also display information such as the time.

When the measurement apparatus 20 functions as a mobile phone, the audio output interface 25 outputs the voice of the other party in a telephone call. When the measurement apparatus 20 is used to measure biological information, the audio output interface 25 can output sound at times such as when the measurement apparatus 20 starts measuring biological information and when the measurement is complete, thereby notifying the user of the start and completion of measurement. The audio output interface 25 may output sound to notify the user that measurement is in progress. By hearing the sound outputted from the audio output interface 25, the user can confirm whether the biological information is being measured properly.

In the example illustrated in FIG. 3A, the operation key portion 29 is configured by operation keys 29A, 29B, 29C. The number and arrangement of the operation key portion 29 are not limited to the example in FIG. 3A. Various numbers and arrangements may be adopted in accordance with the specifications or the like of the measurement apparatus 20. For example, the operation key portion 29 is only provided on the front of the measurement apparatus 20 in the example illustrated in FIG. 3A but may be provided on the side or back of the measurement apparatus 20. In the measurement apparatus 20, the operation key portion 29 may be a switch such as a button for starting measurement of biological information.

The microphone 30 detects the voice of the user or the like mainly when the measurement apparatus 20 functions as a mobile phone, as described above. In the example illustrated in FIG. 3A, only one microphone 30 is provided on the front of the measurement apparatus 20. However, various numbers and arrangements of microphones 30 may be adopted in accordance with the specifications or the like of the measurement apparatus 20.

The measurement apparatus 20 includes an abutting portion 40 and a support 50 on the back side, as illustrated in FIG. 3B. In the example in FIG. 3B, the abutting portion 40 and the support 50 are nearly coplanar with the back surface of the housing 31. At least one of the abutting portion 40 and the support 50, however, may be a member that projects from the back surface of the housing 31. As illustrated in FIG. 3B, the abutting portion 40 and the support 50 are fixed to the measurement apparatus 20 at the back surface of the housing 31. At least one of the abutting portion 40 and the support 50 may, for example, be provided so as not to be detachable from the measurement apparatus 20. At least one of the abutting portion 40 and the support 50 may, for example, be configured to be detachable from the measurement apparatus 20.

The abutting portion 40 and the support 50 are fixed to the back surface of the housing 31 to extend linearly in the direction of the short sides of the back surface. The length of the abutting portion 40 and the support 50 in the direction of the short sides of the back surface of the housing 31 may, for example, be less than the length of the short sides of the back surface of the housing 31. The relationship between the lengths of the abutting portion 40 and the support 50 in the direction of the short sides of the back surface of the housing 31 can be determined as needed. For example, the length of the abutting portion 40 may be greater or less than the length of the support 50 in the direction of the short sides of the back surface of the housing 31. The length of the abutting portion 40 and the length of the support 50 in the direction of the short sides of the back surface of the housing 31 may be equal.

The abutting portion 40 abuts the measured part during measurement of the biological information by the measurement apparatus 20. For example, the abutting portion 40 abuts the user's torso, which is the measured part, during measurement of the biological information. As illustrated in FIG. 3B, the gyro sensor 23 is attached to the back side of the abutting portion 40. The gyro sensor 23 is provided inside the housing 31 in the example in FIG. 3B and is therefore indicated by a dashed line. The abutting portion 40 and the gyro sensor 23 may be configured as separate members or as the same member.

The support 50 abuts against the user at a different position than the abutting portion 40 when biological information is measured by the measurement apparatus 20. For example, the support 50 abuts against the user's torso at a different position than the abutting portion 40. By abutting against the user, the support 50 supports the abutment of the abutting portion 40 against the measured part. The measurement apparatus 20 may include a plurality of supports 50. The plurality of supports 50 may, for example, be arranged linearly. The abutting portion 40 and the support 50 (and also the housing 31) are configured so that change in the measured part abutted by the abutting portion 40 is appropriately transmitted to the gyro sensor 23. Details of the abutment state of the abutting portion 40 and the support 50 against the measured part are provided below.

The measurement apparatus 20 is not limited to the structure illustrated in FIG. 3. As described above, components other than essential components may be omitted from the measurement apparatus 20, or other components may be added, as necessary.

Next, the process for the measurement apparatus 20 to measure biological information is described. The measurement apparatus 20 acquires a motion factor while the abutting portion 40 fixed to the measurement apparatus 20 is abutted against the measured part. The measurement apparatus 20 measures biological information based on the acquired motion factor. The measurement apparatus 20 may acquire the motion factor while the support 50 fixed to the measurement apparatus 20 is abutted against the user at a different position than the measured part.

To measure the biological information, the measurement apparatus 20 enters a state capable of the process to measure biological information based on an input operation by the user, for example. The state capable of the process to measure biological information refers to a state in which an application for measuring biological information has been launched, for example. The user places the measurement apparatus 20 in the state capable of the process to measure biological information and starts acquisition of the motion factor by the measurement apparatus 20. In the present embodiment, the user may place the measurement apparatus 20 in the state capable of the process to measure biological information either before or after inserting the measurement apparatus 20 in the holding portion 13.

Figure 4:
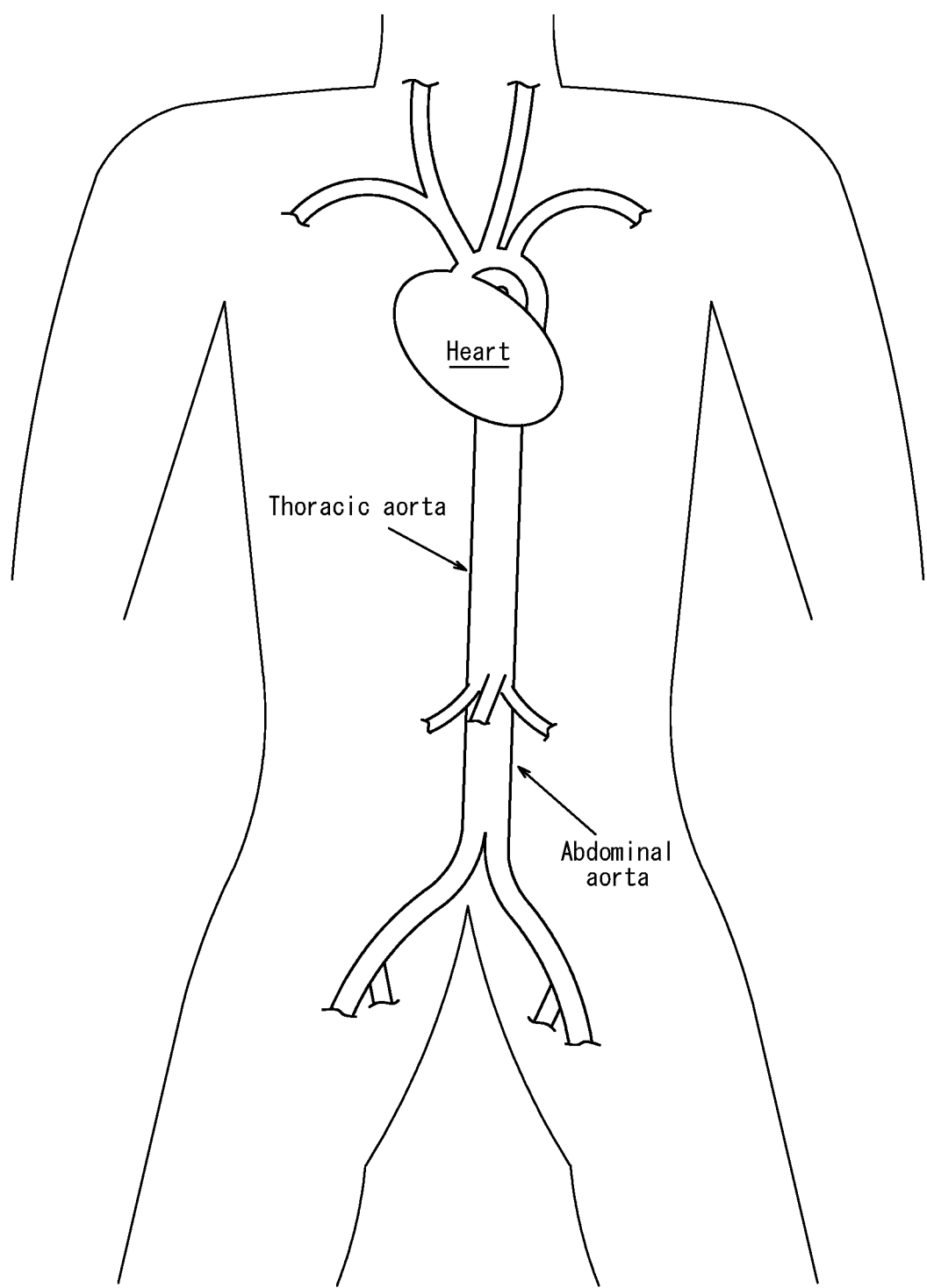
FIG. 4 schematically illustrates the aorta in a human body.

Next, the principle by which the measurement apparatus 20 measures biological information of the user is further explained. The measurement apparatus 20 measures biological information based on change in the user's torso. FIG. 4 schematically illustrates the internal structure of the human body. FIG. 4 schematically illustrates the inner structure of a portion of the human body. In particular, FIG. 4 schematically illustrates a portion of the heart and the aorta in the human body.

The blood inside the human body is supplied to each part of the human body through the blood vessels after being pumped out from the heart. As illustrated in FIG. 4, a portion of the blood pumped out from the heart in the human body passes through the thoracic aorta and then through the abdominal aorta. When blood is pumped from the heart into the thoracic aorta or the abdominal aorta, these blood vessels change, for example by contracting. These changes are transmitted inside the user's body, and the user's torso also changes. Accordingly, the gyro sensor 23 can detect changes in the user's torso due to changes in blood vessels while the measurement apparatus 20 is pressed against the torso, which includes the user's chest or abdomen. The gyro sensor 23 can thus detect a motion factor due to change in the user's torso.

FIGS. 5A and 5B illustrate examples of how the measurement apparatus 20 acquires a motion factor. The holding portion 13 that holds the measurement apparatus 20 is omitted from FIGS. 5A and 5B. FIG. 5A illustrates an example in which the measurement apparatus 20 includes the gyro sensor 23 (built into the main body, for example). FIG. 5B illustrates an example in which the gyro sensor 23 is not built into the main body of the measurement apparatus 20, but rather a member such as an external case or attachment includes the gyro sensor 23.

FIGS. 5A and 5B are cross-sections of a part including the aorta in an organism such as a human body, for example. FIGS. 5A and 5B illustrate a state in which the back side of the housing 31 of the measurement apparatus 20 illustrated in FIGS. 3A and 3B is abutted against the measured part of the organism. Accordingly, as illustrated in FIGS. 5A and 5B, the abutting portion 40 and the support 50 each abut against the measured part of the surface (skin) of the organism. The aorta illustrated in FIGS. 5A and 5B may be the thoracic aorta or the abdominal aorta illustrated in FIG. 4.

As illustrated in FIGS. 5A and 5B, the user presses the measurement apparatus 20 against the torso to cause the measurement apparatus 20 to acquire a motion factor. In a state in which the measurement apparatus 20 and the user's torso are in contact, the abutting portion 40 abuts against the measured part, as illustrated in FIGS. 5A and 5B. The support 50 abuts against the user's torso at a different position than the abutting portion 40 while the measurement apparatus 20 is acquiring the motion factor, as illustrated in FIGS. 5A and 5B.

When the measurement apparatus 20 is abutted against the torso at the position of the arrow P and pressed in the direction of the arrow P, the measurement apparatus 20 is displaced in accordance with the expanding and contracting movement of the blood vessel based on the user's pulsation, as illustrated in FIGS. 5A and 5B. With the support 50 abutted against the torso as a fulcrum, the measurement apparatus 20 is displaced so that the upper end that is not pressed in the direction of the arrow P rotates in a side view, as indicated by the arrow Q in FIGS. 5A and 5B. This displacement is normally vibration in which partial back-and-forth rotational motion is repeated. The gyro sensor 23 in the measurement apparatus 20 acquires the user's pulse wave by detecting displacement of the measurement apparatus 20. The pulse wave refers to a waveform representation of the temporal change in volume of a blood vessel due to inflow of blood, acquired from the body surface.

In this way, the gyro sensor 23 in the measurement apparatus 20 can detect a motion factor due to change in the user's torso. The gyro sensor 23 detects the motion factor due to change in the user's torso while the measurement apparatus 20 is pressed against the user's torso. The controller 21 performs the process to measure biological information of the user based on the motion factor detected by the gyro sensor 23 in this way.

The user's torso may include the user's abdomen or chest. An example of the change in the user's torso being the movement of a blood vessel of the user has been illustrated in FIGS. 5A and 5B, but this example is not limiting. The change in the user's torso may include not only the change produced by movement of the user's blood vessels but also at least one of the change produced by the user's respiration and the change produced by the user's body movement. The user's blood vessels may include the user's aorta. The user's aorta may include at least one of the user's abdominal aorta and thoracic aorta. A large amount of blood continuously flows in a large blood vessel such as the aorta. Therefore, the measurement apparatus 20 can measure the biological information accurately and stably when the user's aorta is the object of measurement.

As illustrated in FIG. 5B, the gyro sensor 23 can easily follow the change in the user's torso by being pressed against the user's torso via an elastic member 32. The measurement apparatus 20 can therefore measure the biological information accurately and stably. Here, the elastic member 32 may be any member that produces an elastic force, such as a spring, rubber, flexible resin, a member using hydraulic pressure such as oil pressure or water pressure, or a member using air pressure. The support 50 illustrated in FIG. 5B connects a housing in which the gyro sensor 23 is provided with a housing in which the gyro sensor 23 is not provided. As illustrated in FIG. 5B, the housing in which the gyro sensor 23 is provided has a mechanism allowing movement, with the support 50 as an axis, relative to the housing in which the gyro sensor 23 is not provided.

As described above, the measurement apparatus 20 illustrated in FIG. 5B can be configured so that the gyro sensor 23 is not built into the main body. In this case, an external member such as an attachment, illustrated in FIG. 5B, that includes the gyro sensor 23 and the abutting portion 40 may be mounted onto the measurement apparatus 20 via the support 50. The detection signal detected by the gyro sensor 23 may, for example, be provided to the controller 21 of the measurement apparatus 20 via the support 50 or the like in this configuration.

By including the gyro sensor 23, the measurement apparatus 20 can measure biological information while being held inside the holding portion 13. At this time, a clothed user can measure biological information from above the clothing. The user does not need to touch the measurement apparatus 20 directly against the skin. It is therefore easy to measure biological information with the measurement apparatus 20.

A known acceleration sensor is inappropriate for use as a pulse wave sensor due to excessive noise. In particular, a miniature acceleration sensor built into a small terminal is not typically used to measure a low-frequency wave around 1 Hz, such as a pulse wave or respiration. Normally, a large acceleration sensor is necessary for such a purpose.

By contrast, the gyro sensor 23 is used to measure biological information in the measurement apparatus 20. The noise during measurement is typically small with a gyro sensor. A gyro sensor is continually vibrating (in the case of a vibration-type gyro sensor) and is therefore structured to allow a reduction in noise. Furthermore, the gyro sensor 23 adoptable in the measurement apparatus 20 can be built into a miniature housing 31.

Next, forms of abutment of the measurement apparatus 20 against the user's torso are described. FIGS. 6A, 6B, and 6C illustrate example forms of abutment of the measurement apparatus 20 against the user's torso. In FIGS. 6A, 6B, and 6C, the gyro sensor 23 built into the measurement apparatus 20 is indicated by dashed lines. To simplify the explanation, the user and the measurement apparatus 20 are depicted in FIGS. 6A, 6B, and 6C, whereas the holding instrument 10 is not depicted.

FIG. 6A illustrates an example of measuring biological information using a measurement apparatus 20 like the one illustrated in FIGS. 3A and 3B. With the measurement apparatus 20 held in the holding portion 13, the subject holds the holding instrument 10. In this state, the abutting portion 40 of the measurement apparatus 20 is pressed against the measured part, and biological information is measured by the measurement apparatus 20.

To allow the gyro sensor 23 to detect movement of the blood vessels well when the measurement apparatus 20 is pressed against the torso, the holding instrument 10 may be configured so that the position of the gyro sensor 23 is not pressed against the torso by the main body 11 of the holding instrument 10. In this case, the holding instrument 10 may be configured so that a position where the gyro sensor 23 is not located, i.e. near the lower end of the measurement apparatus 20 illustrated in FIG. 3A, is pressed against the torso. The support 50 illustrated in FIG. 3B is located at the back near the lower end of the measurement apparatus 20 illustrated in FIG. 3A.

When the measurement apparatus 20 is pressed against the torso, the user can freely change the measured part abutted by the abutting portion 40 of the measurement apparatus 20 by changing the way the user embraces the holding instrument 10. The user can, for example, make it easy to detect movement of the thoracic aorta by moving the holding instrument 10 towards the upper body. The user can, for example, make it easy to detect movement of the abdominal aorta by moving the holding instrument 10 towards the lower body. In this way, the user of the holding instrument 10 can very accurately measure biological information by searching for the position of the measured part where the biological information can be measured well.

FIG. 6B illustrates an example in which the user is wearing a belt or a waistband. When the user is wearing a belt 60, waistband 62, or the like, as illustrated in FIG. 6B, then a portion of the measurement apparatus 20 may be pressed against the user's torso while at least a portion other than this portion of the measurement apparatus 20 is pressed against the belt 60 or waistband 62 of the user's clothing. In this state, the gyro sensor 23 may detect the motion factor. The controller 21 may perform the measurement process based on the motion factor detected in this way.

FIG. 6C illustrates an example of the measurement apparatus 20 illustrated in FIG. 6A being used while turned upside down. In the example in FIG. 6C, movement of the abdominal aorta is easier to detect than in the examples in FIGS. 6B and 6C. In this case, the abutting portion 40 of the measurement apparatus 20 is pressed against the measured part while the user is embracing the holding instrument 10.

In this way, a portion of the measurement apparatus 20 in an embodiment may be pressed against the lower abdomen side of the user's torso while at least a portion other than this portion of the measurement apparatus 20 is pressed towards the top of the user's torso from the lower abdomen side. In this state, the gyro sensor 23 may detect the motion factor. The controller 21 may perform the measurement process based on the motion factor detected in this way.

Figure 7A:
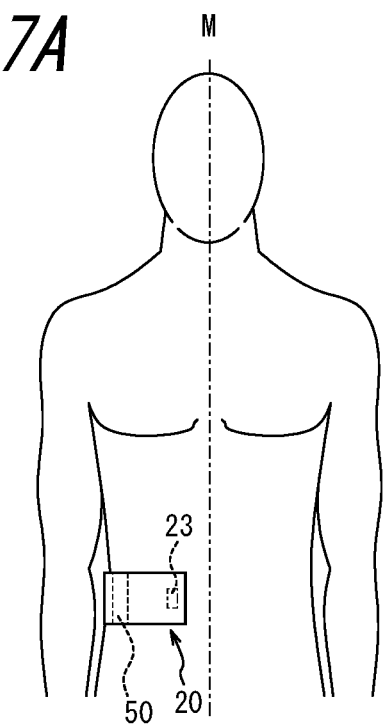
FIGS. 7A and 7B illustrate forms of abutment of the measurement apparatus against the torso of a user.
Figure 7B:
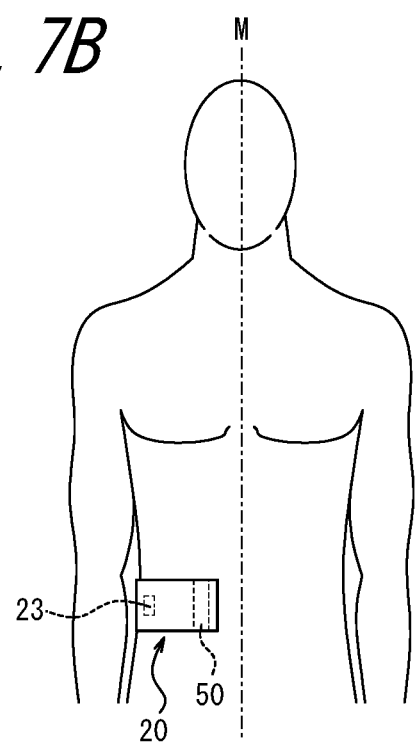

Like FIGS. 6A, 6B, and 6C, FIGS. 7A and 7B illustrate other example forms of abutment of the measurement apparatus 20 against the user's torso. In FIGS. 7A and 7B as well, the gyro sensor 23 built into the measurement apparatus 20 is indicated by dashed lines.

As illustrated in FIG. 7A, the measurement apparatus 20 may be pressed against the torso while facing sideways. To allow the gyro sensor 23 to detect movement of the blood vessels well when the measurement apparatus 20 is pressed against the torso while in the state illustrated in FIG. 7A, the holding instrument 10 may be configured so that the position of the gyro sensor 23 is not pressed. In this case, the holding instrument 10 may be configured so that a position where the gyro sensor 23 is not located, i.e. near the end of the measurement apparatus 20 at the side of the support 50, is pressed against the torso. The gyro sensor 23 comes closer to the centerline (midline) M of the torso in this case, thereby allowing movement of the thoracic aorta or the abdominal aorta to be detected well.

As illustrated in FIG. 7B, the measurement apparatus 20 may be oriented in the opposite direction from the case in FIG. 7A. In this case, the gyro sensor 23 abuts against the side of the torso, i.e. near the side of the abdomen. A position where the gyro sensor 23 is not located, i.e. near the end of the measurement apparatus 20 at the side of the support 50, may be pressed against the torso in this case.

In this way, a portion of the measurement apparatus 20 in an embodiment may be pressed against the side of the user's torso while at least a portion other than this portion of the measurement apparatus 20 is pressed towards the midline M of the user's torso from the side of the torso. In this state, the gyro sensor 23 may detect the motion factor. The controller 21 may perform the measurement process based on the motion factor detected in this way.

Figure 8:
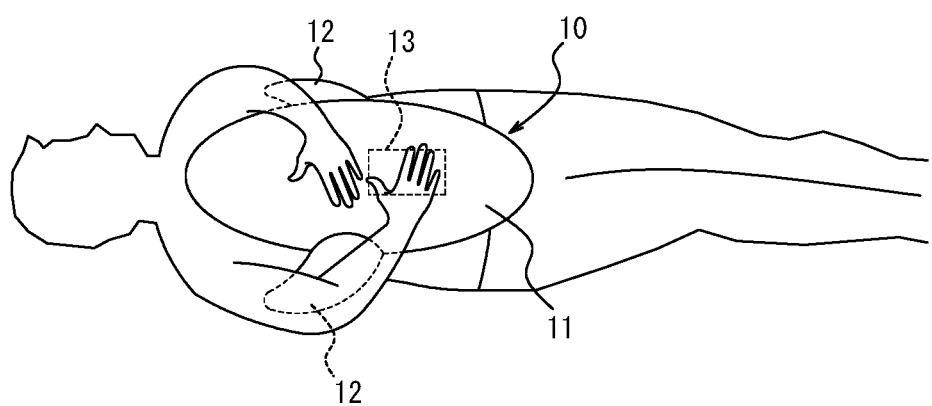
FIG. 8 illustrates an example mode of use of the holding instrument of FIGS. 1A and 1B.

Next, the way in which the measurement apparatus 20 measures the biological information is described for the case of using the holding instrument 10. FIG. 8 illustrates an example mode of use of the holding instrument 10.

The user inserts the measurement apparatus 20 in the holding portion 13 when using the measurement apparatus 20 to measure the biological information. At this time, the measurement apparatus 20 is held in the holding portion 13 so that the abutting portion 40 of the measurement apparatus 20 faces the front of the holding instrument 10. When the measurement apparatus 20 is held in this way, the abutting portion 40 abuts against the user's torso while the user is embracing the holding instrument 10. The user may place the measurement apparatus 20 in a state capable of measuring the biological information either before or after inserting the measurement apparatus 20 in the holding portion 13. In the present embodiment, the user is assumed to place the measurement apparatus 20 in a state capable of measuring the biological information after inserting the measurement apparatus 20 in the holding portion 13.

The user embraces the holding instrument 10 while the measurement apparatus 20 is held in the holding portion 13. At this time, the user embraces the holding instrument 10 so that the holding portion 13 abuts against the measured part. When the user embraces the holding instrument 10 in this way, the measurement apparatus 20 is held in the holding portion 13 with the abutting portion 40 facing the front of the holding instrument 10. The abutting portion 40 therefore abuts against the user's torso. The user may embrace the holding instrument 10 so that the abutting portion 40 abuts against the measured part. The user may embrace the holding instrument 10 in a seated position, or as illustrated in FIG. 8, in a supine position.

The arms 12 of the holding instrument 10 may bend to wrap around the user's torso (for example, the abdomen) while the user is embracing the holding instrument 10. The contact state between the holding instrument 10 and the user is more easily maintained when the arms 12 wrap around the user's torso, even if the user is not embracing the holding instrument 10 tightly. The abutment state of the abutting portion 40 against the measured part is therefore more easily maintained.

By the principle described with reference to FIG. 5, the measurement apparatus 20 detects a motion factor of the user and measures the biological information while the user is embracing the holding instrument 10.

Figure 9:
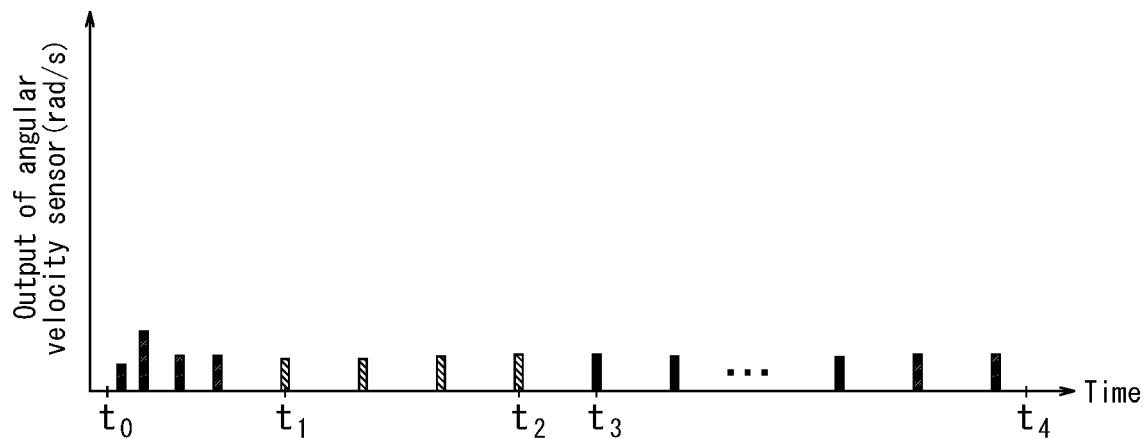
FIG. 9 schematically illustrates a process of measuring a pulse wave with the measurement apparatus.
Figure 10:
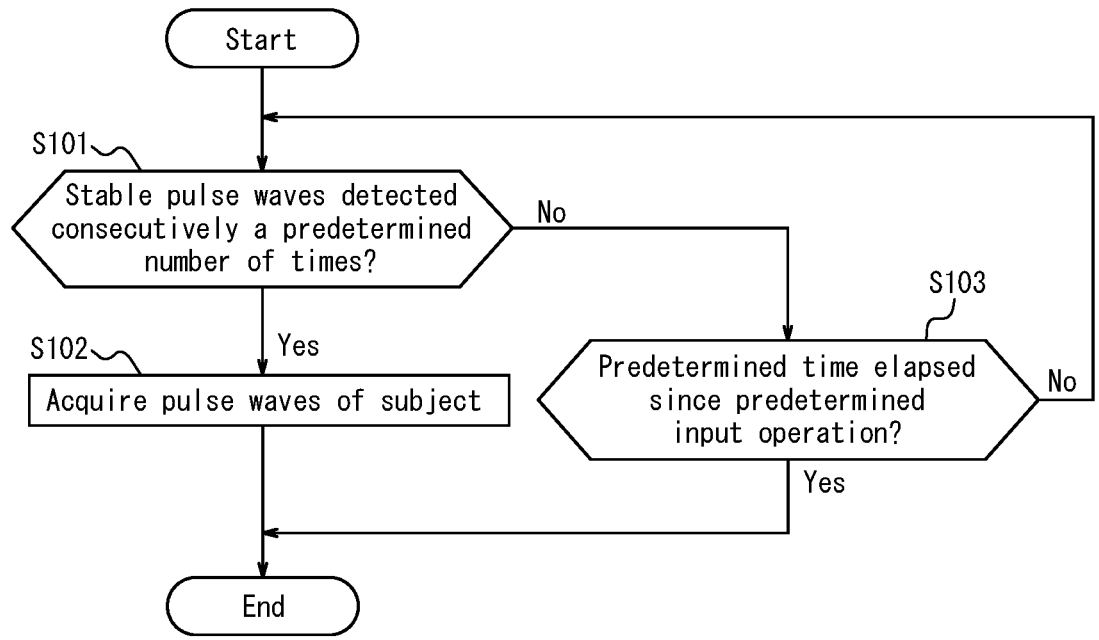
FIG. 10 is a flowchart illustrating the procedure for measuring the pulse wave with the measurement apparatus.

FIG. 9 schematically illustrates the process of measuring a pulse wave with the measurement apparatus 20. FIG. 10 is a flowchart illustrating the procedure for measuring the pulse wave with the measurement apparatus 20. In FIG. 9, the horizontal axis represents time, and the vertical axis schematically represents pulse wave-based output (rad/s) of the angular velocity sensor, i.e. the gyro sensor 23. FIG. 9 only shows the peak of each pulse wave in the output of the angular velocity sensor.

It is assumed that the user performs a predetermined input operation to the measurement apparatus 20 to start pulse wave measurement at time to. In other words, it is assumed that the measurement apparatus 20 becomes capable of measuring the biological information and begins measuring the pulse wave at time to. After performing the predetermined input operation to start pulse wave measurement, the user embraces the holding instrument 10 and places the abutting portion 40 against the measured part, as illustrated in FIG. 8.

Upon starting the pulse wave measurement, the controller 21 in the measurement apparatus 20 detects output of the gyro sensor 23 corresponding to movement of the user's blood vessels. For a predetermined time period immediately after the start of measurement (from time to $t_0$ time $t_1$ in FIG. 9), the user adjusts the position at which the holding instrument 10 is embraced, thereby adjusting the abutment state of the abutting portion 40 against the measured part. The measurement apparatus 20 cannot accurately acquire the pulse wave during this predetermined time period, because the output of the gyro sensor 23 is unstable. The measurement apparatus 20 therefore need not use the pulse wave measured during this time period in the measurement of blood components, which are an example of biological information. The measurement apparatus 20 need not store the pulse wave measured during this time period in the storage 28, for example.

The controller 21 judges whether stable pulse waves have been detected consecutively a predetermined number of times after the start of pulse wave measurement (step S101 of FIG. 10). The predetermined number of times is four in the example in FIG. 9, but this example is not limiting. Stable pulse waves refer, for example, to the variation in the peak output of each pulse wave and/or the variation in the intervals between peaks of pulse waves being within a predetermined error range. The predetermined error range in the intervals between peaks may be, but is not limited to, 150 msec. FIG. 9 illustrates an example of the case of the controller 21 detecting pulse waves from time $t_1$ to time $t_2$, with the variation in the intervals between peaks of the pulse waves being within ±150 msec four times consecutively.

When the controller 21 judges that stable pulse waves have been detected consecutively a predetermined number of times after the start of pulse wave measurement (step S101 of FIG. 10: Yes), the controller 21 begins acquiring pulse waves (step S102). In other words, the controller 21 acquires pulse waves used to measure blood components. The start time of pulse wave acquisition is time $t_3$ in FIG. 9, for example. The controller 21 may store the pulse waves acquired in this way in the storage 28. In this way, the measurement apparatus 20 starts to acquire pulse waves when it is judged that stable pulse waves have been detected consecutively a predetermined number of times. This facilitates prevention of erroneous detection in cases such as when the abutting portion 40 is not properly abutting against the measured part.

After starting to acquire pulse waves, the controller 21 stops acquiring pulse waves when an ending condition for pulse wave acquisition is satisfied. The ending condition may, for example, be when a predetermined time has elapsed after the start of pulse wave acquisition. The ending condition may, for example, be when pulse waves of a predetermined number of pulse beats have been acquired. The ending condition is not limited to these examples. Any appropriate condition may be set. In the example in FIG. 9, the controller 21 stops acquiring pulse waves at time $t_4$, when a predetermined time (such as 8 sec or 15 sec) has elapsed from time $t_3$. The flow in FIG. 10 thus ends.

When the controller 21 judges that stable pulse waves have not been detected consecutively a predetermined number of times after the start of pulse wave measurement (step S101 of FIG. 10: No), the controller 21 judges whether a predetermined time has elapsed from when the predetermined input operation for starting pulse wave measurement was performed (step S103).

When the controller 21 judges that a predetermined time (for example, 30 sec) has not elapsed from when the predetermined input operation for starting pulse wave measurement was performed (step S103: No), the flow of FIG. 10 proceeds to step S101.

When the controller 21 judges that stable pulse waves cannot be detected despite a predetermined time having elapsed from when the predetermined input operation for starting pulse wave measurement was performed (step S103: Yes), the measurement process automatically ends (times out), and the flow of FIG. 10 ends.

Figure 11:
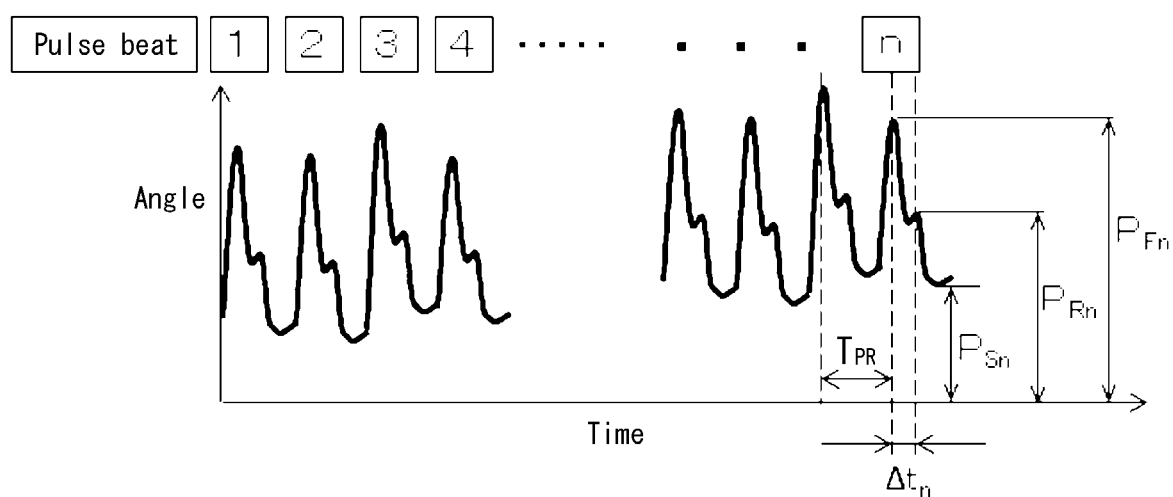
FIG. 11 illustrates an example of pulse waves acquired by a sensor.

FIG. 11 illustrates an example of pulse waves acquired at the measured part (torso) using the measurement apparatus 20. FIG. 11 illustrates the case where the gyro sensor 23 is used as the means for detecting pulsation. FIG. 11 is the result of integrating the angular velocity acquired by the angular velocity sensor, i.e. the gyro sensor 23. The horizontal axis in FIG. 11 represents time, and the vertical axis represents the angle. Since the acquired pulse wave may, for example, include noise that is due to body movement of the user, the pulse wave may be corrected by a filter that removes the direct current (DC) component, so as to extract only the pulsation component.

The measurement apparatus 20 calculates a pulse wave index from the acquired pulse wave and uses the pulse wave index to measure blood components. A method for calculating a pulse wave index from the acquired pulse wave is described with reference to FIG. 11. Propagation of the pulse wave is a phenomenon in which pulsation due to blood being pumped from the heart is transmitted through artery walls or blood. The pulsation due to blood pumped from the heart reaches the peripheries of limbs as a forward wave, a portion of which is reflected at locations such as where a blood vessel branches, or where the diameter of a blood vessel changes, and returns as a reflected wave. The pulse wave index is, for example, the pulse wave velocity (PWV) of the forward wave, the magnitude PR of the reflected wave of the pulse wave, the time difference Δt between the forward wave and the reflected wave of the pulse wave, or the augmentation index (AI) represented as the ratio between the magnitudes of the forward wave and the reflected wave of the pulse wave.

The pulse wave illustrated in FIG. 11 represents n pulse beats of the user, where n is an integer and is equal to or greater than one. The pulse wave is a combined wave, in which the forward wave generated by ejection of blood from the heart overlaps with the reflected wave generated at blood vessel branches and locations of change in blood vessel diameter. In FIG. 11, the magnitude of the peak in the pulse wave from the forward wave in each pulse beat is labeled $P_{Fn}$, the magnitude of the peak in the pulse wave from the reflected wave in each pulse beat is labeled $P_{Rn}$, and the smallest value of the pulse wave in each pulse beat is labeled $P_{Sn}$. In FIG. 11, the interval between peaks of the pulse beat is labeled $T_{PR}$.

The pulse wave index includes a quantification of information obtained from the pulse wave. An example of a pulse wave index is PWV, which is calculated in accordance with the difference in propagation time of pulse waves measured at two points, such as the upper arm and ankle, and the distance between the two points. In greater detail, PWV is calculated by synchronously acquiring the pulse wave at two points on an artery (e.g. the upper arm and ankle) and dividing the distance between the two points (L) by the time difference of the pulse waves at the two points (PTT). A further example of a pulse wave index is the reflected wave magnitude PR, which may be calculated as the magnitude $P_{Rn}$ of the peak in the pulse wave from the reflected wave or as the average of n values, $P_{Rave}$. A further example of a pulse wave index is the time difference Δt between the forward wave and the reflected wave of the pulse wave, which may be calculated as the time difference Δtn between predetermined pulse beats or as the average of n time differences, $\Delta t_{ave}$. A further example of a pulse wave index is the AI, which is the result of dividing the magnitude of the reflected wave by the magnitude of the forward wave and is represented as $AI_n=(P_{Rn}-P_{Sn})/(P_{Fn}-P_{Sn})$. $AI_n$ is the AI for each pulse beat. As a pulse wave index, AI may, for example, be calculated by measuring the pulse wave for several seconds and calculating the average $AI_{ave}$ of the $AI_n$ for each pulse beat (n=an integer from 1 to n).

The PWV, the reflected wave magnitude $P_R$, the time difference Δt between the forward wave and the reflected wave, and the AI indices can be used to estimate the state of arteriosclerosis because they change depending on the hardness of the blood vessel walls. The PWV increases, for example, if the blood vessel walls are hard. The reflected wave magnitude $P_R$, for example, also increases if the blood vessel walls are hard. The time difference Δt between the forward wave and the reflected wave, for example, decreases if the blood vessel walls are hard. The AI, for example, increases if the blood vessel walls are hard. Furthermore, by using of these indices that are based on the pulse wave, the measurement apparatus 20 can estimate the state of arteriosclerosis and also estimate the blood fluidity (viscosity). In particular, the measurement apparatus 20 can estimate the change in blood fluidity from the change in indices based on pulse waves acquired for the same measured part of the same user during a time period (such as several days) over which the state of arteriosclerosis exhibits essentially no change. Here, blood fluidity indicates the ease of blood flow. The PWV, for example, decreases if the blood fluidity is low. The reflected wave magnitude $P_R$, for example, also decreases if the blood fluidity is low. The time difference Δt between the forward wave and the reflected wave, for example, increases if the blood fluidity is low. The AI, for example, decreases if the blood fluidity is low.

In the present embodiment, as an example of pulse wave indices, the measurement apparatus 20 calculates the PWV, the reflected wave magnitude $P_R$, the time difference $\Delta t$ between the forward wave and the reflected wave, and the AI. However, the pulse wave indices are not limited to these examples. For example, the measurement apparatus 20 may use posterior systolic blood pressure as a pulse wave index.

Figure 12:
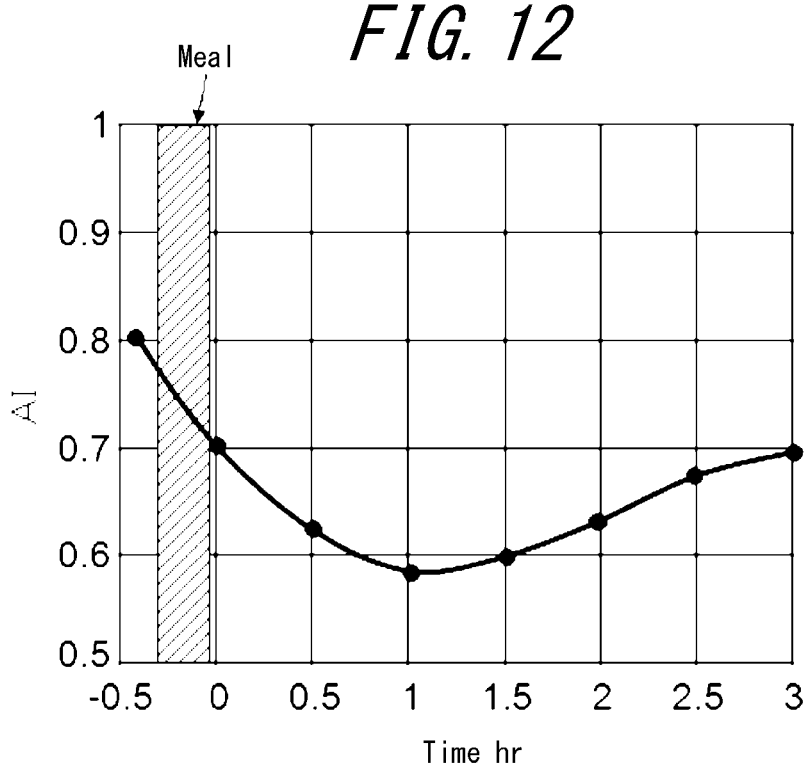
FIG. 12 illustrates the change over time in calculated AI.

FIG. 12 illustrates the change over time in the calculated AI. In an embodiment, the pulse wave is acquired for approximately five seconds using the measurement apparatus 20 provided with an angular velocity sensor. The controller 21 calculates the AI from the acquired pulse wave for each pulse beat and further calculates the average $AI_{ave}$ thereof. In an embodiment, the measurement apparatus 20 acquires the pulse wave at a plurality of times before a meal and after the meal and calculates the average AI (simply "AI" below) as an example of an index based on the acquired pulse wave. The horizontal axis in FIG. 12 represents elapsed time, with the initial measured time after a meal as 0. The vertical axis in FIG. 12 indicates the AI calculated from the pulse waves acquired at that time.

The measurement apparatus 20 acquired the pulse waves before a meal, immediately after the meal, and every 30 minutes after the meal and calculated a plurality of AI values on the basis of the pulse waves. The AI calculated from the pulse wave acquired before the meal was approximately 0.8. The AI immediately after the meal was lower than before the meal, and the AI reached its lowest value approximately one hour after the meal. The AI gradually increased in the three hours after the meal, until completion of the measurement.

The measurement apparatus 20 can estimate the change in blood fluidity from the change in the calculated AI. The blood fluidity reduces, for example, when red blood cells, white blood cells, and platelets in the blood harden into balls, or when the adhesive force increases. The blood fluidity also reduces, for example, when the moisture content of platelets in the blood decreases. These changes in the blood fluidity depend on the user's state of health, such as the below-described glycolipid state, heatstroke, dehydration, hypothermia, and the like. Before the user's state of health becomes critical, the user can use the measurement apparatus 20 of an embodiment to learn about the user's own changes in blood fluidity. From the changes in AI before and after a meal as illustrated in FIG. 12, it can be inferred that the blood fluidity decreased after the meal, reaching a minimum approximately one hour after the meal and gradually increasing thereafter. The measurement apparatus 20 may notify the user of a state of low blood fluidity or a state of high blood fluidity. For example, the measurement apparatus 20 may judge the states of low and high blood fluidity taking the average AI for the user's actual age as a standard. The measurement apparatus 20 may judge the blood fluidity to be in a high state when the calculated AI is greater than the average and to be in a low state when the calculated AI is less than the average. The measurement apparatus 20 may, for example, judge the low and high states of blood fluidity taking the preprandial AI as a standard. The measurement apparatus 20 may compare the postprandial AI with the preprandial AI to estimate the degree to which the blood fluidity is in a low state. The measurement apparatus 20 can, for example, use the preprandial AI, i.e. the AI when fasting, as an index of the user's vascular age (blood vessel hardness). By calculating the amount of change in the AI calculated using the user's preprandial AI, i.e. the AI when fasting, as a standard, the measurement apparatus 20 can reduce the estimation error due to the user's vascular age (blood vessel hardness), for example. Hence, the measurement apparatus 20 can more accurately estimate the change in blood fluidity.

Figure 13:
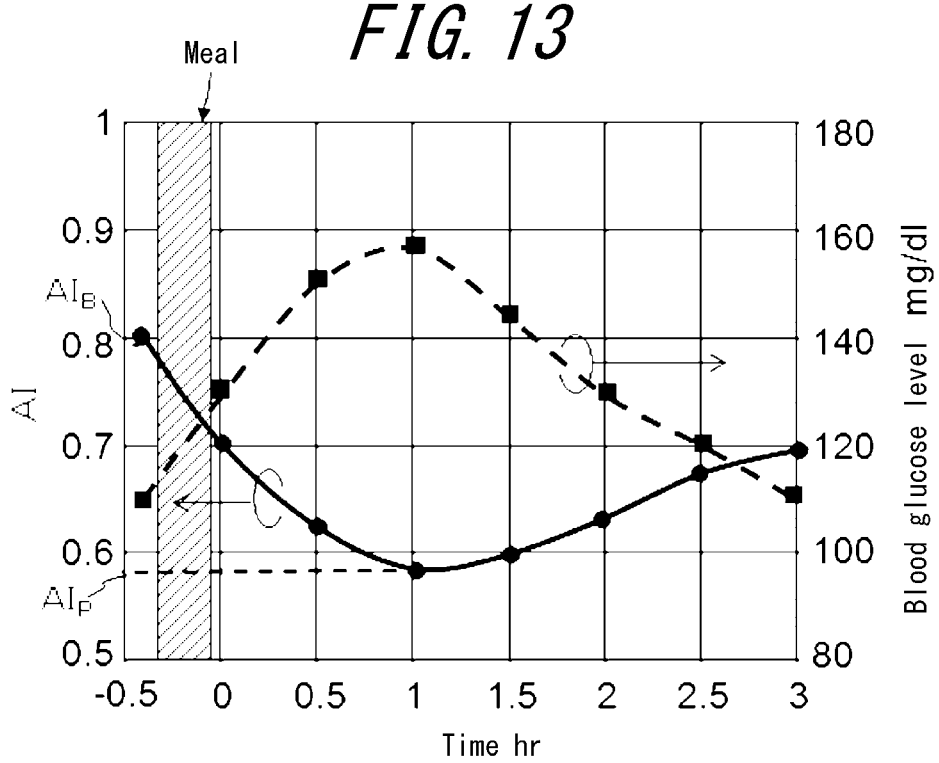
FIG. 13 illustrates the calculated AI and the result of measuring the blood glucose level.

FIG. 13 illustrates the calculated AI and the result of measuring the blood glucose level. The method of acquiring the pulse waves and the method of calculating AI are the same as in the embodiment illustrated in FIG. 12. The right vertical axis in FIG. 13 represents the blood glucose level, and the left vertical axis represents the calculated AI. The solid curve in FIG. 13 indicates the AI calculated from the acquired pulse waves, and the dotted curve indicates the measured blood glucose level. The blood glucose level was measured immediately after the pulse wave was acquired. The blood glucose level was measured using the blood glucose meter Medisafe Fit® (Medisafe Fit is a registered trademark in Japan, other countries, or both) manufactured by Terumo Corporation. As compared to the preprandial blood glucose level, the postprandial blood glucose level rose by approximately 20 mg/dl. The blood glucose level reached the largest value approximately one hour after the meal. Subsequently, until measurement was completed, the blood glucose level reduced slowly and became nearly the same as the preprandial blood glucose level at approximately three hours after the meal.

As illustrated in FIG. 13, the preprandial and postprandial blood glucose levels are negatively correlated with the AI calculated from the pulse wave. As the blood glucose level rises, the red blood cells and white blood cells harden into balls because of sugar in the blood, or the adhesive force increases. As a result, the blood fluidity reduces. Upon a reduction in the blood fluidity, the PWV may decrease. Upon a decrease in the PWV, the time difference $\Delta t$ between the forward wave and the reflected wave may increase. Upon an increase in the time difference $\Delta t$ between the forward wave and the reflected wave, the reflected wave magnitude $P_R$ may decrease relative to the forward wave magnitude $P_F$. Upon a decrease in the reflected wave magnitude $P_R$ relative to the forward wave magnitude $P_F$, the AI may decrease. Since the AI within the several hours flowing the meal (three hours in an embodiment) is correlated with the blood glucose level, variation in the user's blood glucose level can be inferred from a change in AI. If the user's blood glucose level is measured and the correlation with the AI is determined in advance, the measurement apparatus 20 can estimate the user's blood glucose level from the calculated AI.

The measurement apparatus 20 can infer the state of the user's glucose metabolism in accordance with the occurrence time of $AI_P$, which is the first detected local minimum of the AI after a meal. For example, the measurement apparatus 20 estimates the blood glucose level as the state of glucose metabolism. As an example of inferring the state of glucose metabolism, the measurement apparatus 20 can infer that the user has abnormal glucose metabolism (patient with diabetes) when the first detected local minimum $AI_P$ of the AI after a meal is detected after a predetermined length of time or longer (for example, approximately 1.5 hours or longer after a meal).

The measurement apparatus 20 can infer the state of the user's glucose metabolism in accordance with the difference $AI_B$–$AI_P$ between $AI_B$, which is the preprandial AI, and $AI_P$, which is the first detected local minimum of the postprandial AI. As an example of inferring the state of glucose metabolism, the measurement apparatus 20 can infer that the user has abnormal glucose metabolism (patient with postprandial hyperglycemia) when $AI_B$–$AI_P$ is equal to or greater than a predetermined value (for example, 0.5 or higher).

Figure 14:
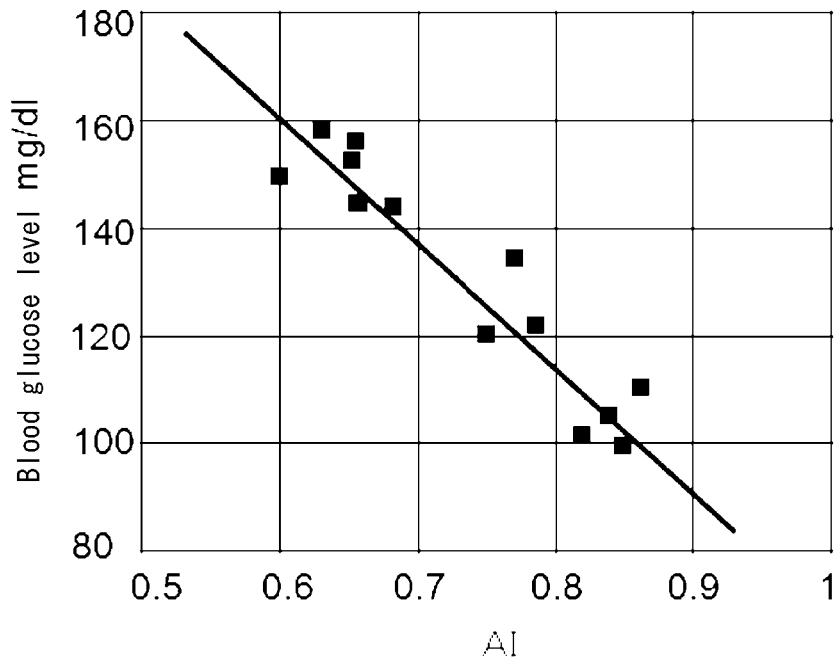
FIG. 14 illustrates the relationship between the calculated AI and the blood glucose level.

FIG. 14 illustrates the relationship between the calculated AI and the blood glucose level. The calculated AI and the blood glucose level were acquired within one hour after a meal, when the blood glucose level varies greatly. The data in FIG. 14 includes a plurality of different data points after a meal for the same user. As illustrated in FIG. 14, the calculated AI and the blood glucose level are negatively correlated. The correlation coefficient between the calculated AI and the blood glucose level is equal to or greater than 0.9. For example, if the correlation between the calculated AI and blood glucose level illustrated in FIG. 14 is determined for each user in advance, the measurement apparatus 20 can also estimate the user's blood glucose level from the calculated AI.

Figure 15:
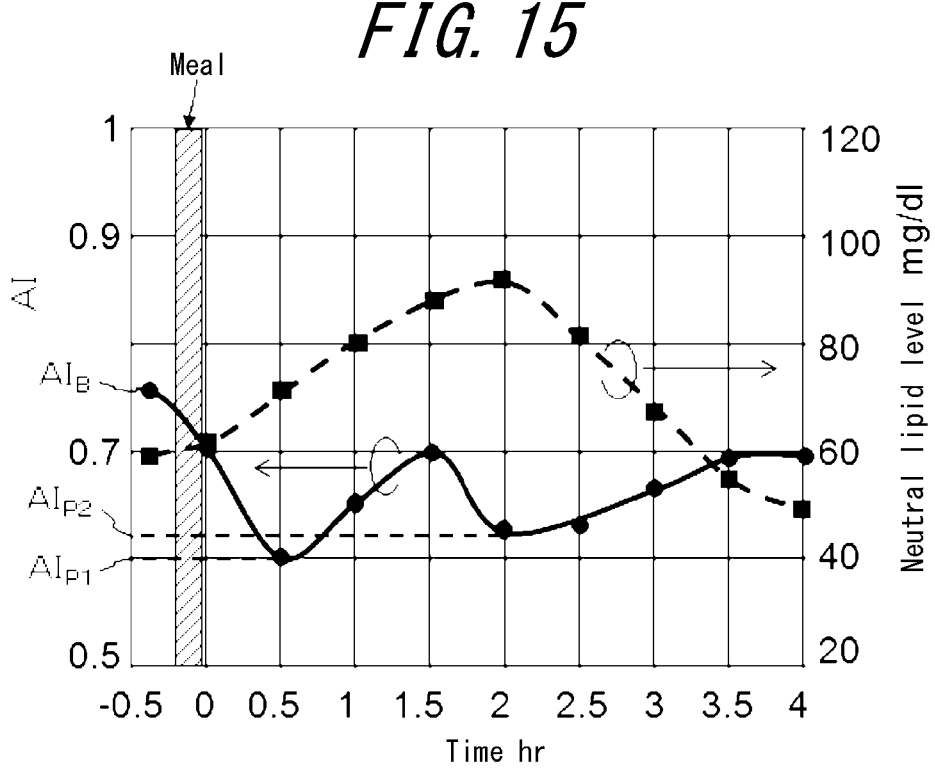
FIG. 15 illustrates the calculated AI and the result of measuring the neutral lipid level.

FIG. 15 illustrates the calculated AI and the result of measuring the neutral lipid level. The method of acquiring the pulse waves and the method of calculating AI are the same as in the embodiment illustrated in FIG. 12. The right vertical axis in FIG. 15 represents the neutral lipid level in the blood, and the left vertical axis represents the AI. The solid curve in FIG. 15 indicates the AI calculated from the acquired pulse waves, and the dotted curve indicates the measured neutral lipid level. The neutral lipid level was measured immediately after the pulse wave was acquired. The neutral lipid level was measured using the "Pocket Lipid" lipid measurement apparatus manufactured by Techno Medica Co., Ltd. As compared to the preprandial neutral lipid level, the highest value of the postprandial neutral lipid level represented a rise of approximately 30 mg/dl. The neutral lipid level reached the highest value approximately two hours after the meal. Subsequently, until measurement was completed, the neutral lipid level decreased slowly and became nearly the same as the preprandial neutral lipid level at approximately three and a half hours after the meal.

By contrast, the local minimums of the calculated AI were a first local minimum $AI_{P1}$ detected approximately 30 minutes after the meal and a second local minimum $AI_{P2}$ detected approximately two hours after the meal. It can be inferred that the first local minimum $AI_{P1}$ detected approximately 30 minutes after the meal is caused by the above-described blood glucose level after the meal. The time at which the second local minimum $AI_{P2}$ was detected is approximately two hours after the meal and is nearly coincident with that of the highest neutral lipid level detected approximately two hours after the meal. From this, it can be inferred that the second local minimum $AI_{P2}$ detected a predetermined length of time or longer after a meal is due to the effect of neutral lipids. Like the blood glucose level, it can be understood that the preprandial and postprandial neutral lipid values are negatively correlated with the AI calculated from the pulse wave. In particular, the local minimum $AI_{P2}$ of the AI calculated a predetermined length of time or longer (in an embodiment, approximately 1.5 hours or longer) after a meal is correlated with neutral lipids. Therefore, the variation in the user's neutral lipid level can be estimated from the variation in AI. If the user's neutral lipid level is measured and the correlation with the AI is determined in advance, the measurement apparatus 20 can estimate the user's neutral lipid level from the calculated AI.

The measurement apparatus 20 can infer the user's state of lipid metabolism based on the occurrence time of the second local minimum $AI_{P2}$ detected a predetermined length of time or longer after a meal. For example, the measurement apparatus 20 estimates the lipid level as the state of lipid metabolism. As an example, the measurement apparatus 20 can infer that the user has abnormal lipid metabolism (patient with hyperlipidemia) when the second local minimum $AI_{P2}$ is detected a predetermined length of time or longer (for example, four hours or longer) after a meal.

The measurement apparatus 20 can infer the user's state of lipid metabolism in accordance with the difference $AI_B-AI_{P2}$ between the $AI_B$, which is the preprandial AI, and the second local minimum $AI_{P2}$ detected a predetermined length of time or longer after the meal. As an example, the measurement apparatus 20 can infer that the user's state of lipid metabolism is abnormal (patient with postprandial hyperlipidemia) when $AI_B-AI_{P2}$ is equal to or greater than 0.5.

From the measurement results illustrated in FIG. 13 through FIG. 15, the measurement apparatus 20 of an embodiment can infer the user's state of glucose metabolism in accordance with the first local minimum $AI_{P1}$, detected earliest after a meal, and the occurrence time thereof. Furthermore, the measurement apparatus 20 can infer the user's state of lipid metabolism in accordance with the second local minimum $AI_{P2}$, detected a predetermined length of time or longer after the first local minimum $AI_{P1}$, and the occurrence time thereof.

The case of neutral lipids has been described as an example of inferring the lipid metabolism, but inference of the lipid metabolism is not limited to neutral lipids. The lipid level estimated by the measurement apparatus 20 includes, for example, total cholesterol, HDL cholesterol, and LDL cholesterol. These lipid values exhibit tendencies similar to the above-described case of neutral lipids.

Figure 16:
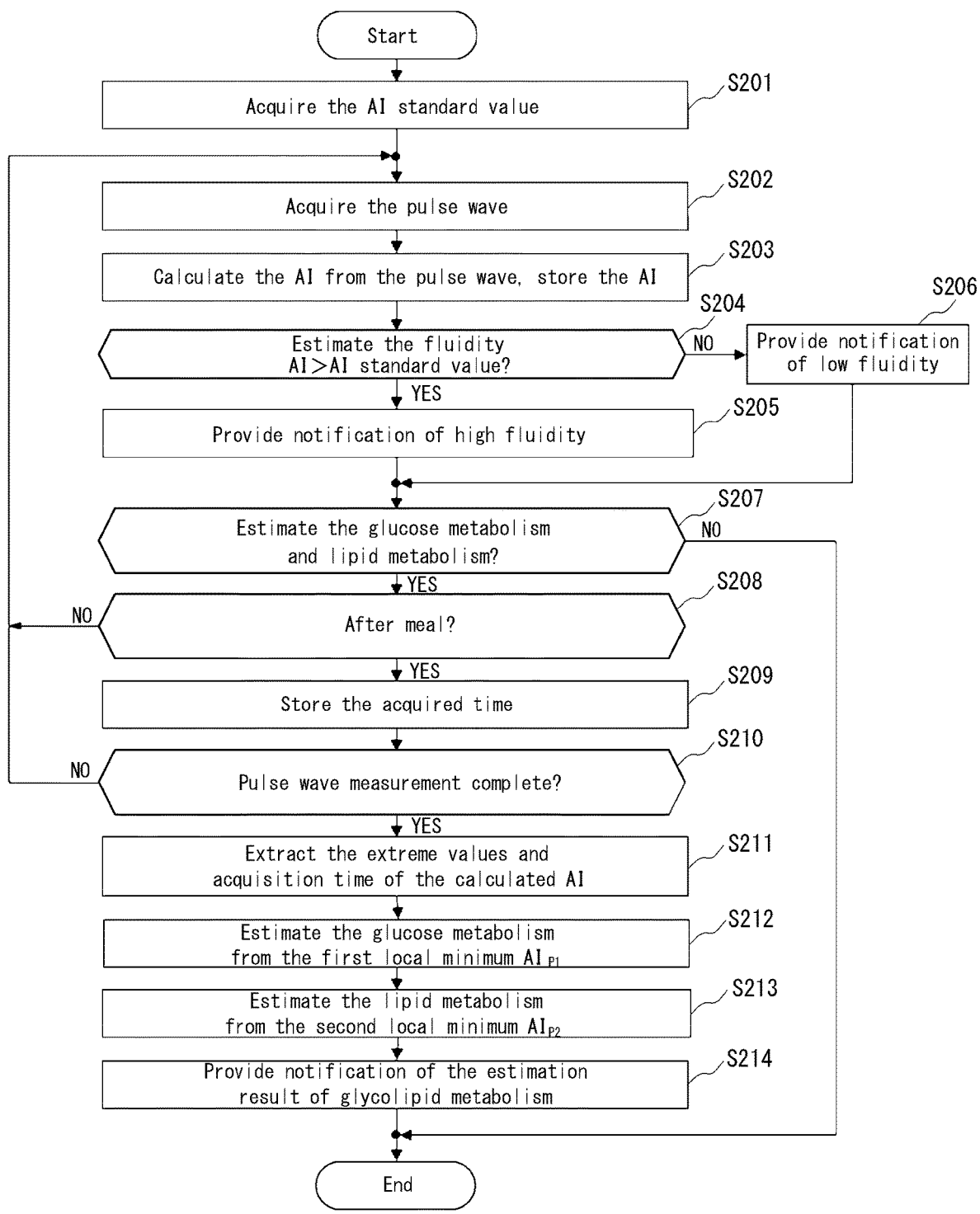
FIG. 16 is a flowchart illustrating the procedure to estimate the blood fluidity and the state of glucose metabolism and lipid metabolism.

FIG. 16 is a flowchart illustrating the procedure for estimating the blood fluidity and the state of glucose metabolism and lipid metabolism based on the AI. With reference to FIG. 16, the process by which the measurement apparatus 20 according to an embodiment estimates the blood fluidity and the state of glucose metabolism and lipid metabolism is described.

As illustrated in FIG. 16, the measurement apparatus 20 acquires the user's AI standard value as an initial setting (step S201). An average AI estimated from the user's age, or the user's AI when fasting as acquired in advance, may be used as the AI standard value. The measurement apparatus 20 may also use the AI judged to be before a meal in steps S202 to S208 or the AI calculated immediately before pulse wave measurement as the AI standard value. In this case, the measurement apparatus 20 executes step S201 after steps S202 to S208.

Subsequently, the measurement apparatus 20 acquires the pulse wave (step S202). For example, the measurement apparatus 20 determines whether a pulse wave of predetermined amplitude or higher has been obtained during a predetermined measurement time (for example, five seconds). If a pulse wave of predetermined amplitude or higher has been obtained, the process proceeds to step S203. If a pulse wave of predetermined amplitude or higher has not been obtained, step S202 is repeated (these steps are not illustrated). In step S202, the measurement apparatus 20 automatically acquires the pulse wave if a pulse wave of predetermined amplitude or higher is detected, for example.

From the pulse wave acquired in step S202, the measurement apparatus 20 calculates the AI as a pulse wave index and stores the AI in the storage 28 (step S203). The measurement apparatus 20 may calculate the average $AI_{ave}$ from the $AI_n$ (n=an integer from 1 to n) for each of a predetermined number of pulse beats (for example, three beats) and use the average $AI_{ave}$ as the AI. Alternatively, the measurement apparatus 20 may calculate the AI for a specific pulse beat.

The AI may, for example, be corrected using the pulse rate $P_R$, the pulse pressure ($P_F-P_S$), or the like. Pulse and AI are known to be negatively correlated, as are pulse pressure and AI. When correcting the AI, the measurement apparatus 20 calculates the pulse and the pulse pressure in addition to the AI in step S203, for example. The measurement apparatus 20 corrects the AI by substituting the acquired pulse, pulse pressure, and the like into a correction formula derived in advance.

Subsequently, the measurement apparatus 20 compares the AI standard value acquired in step S201 with the AI calculated in step S203 and estimates the user's blood fluidity (step S204). When the calculated AI is greater than the AI standard value (YES), it is inferred that the blood fluidity is high. In this case, the measurement apparatus 20 provides notification that the blood fluidity is high, for example (step S205). When the calculated AI is not greater than the AI standard value (NO), it is inferred that the blood fluidity is low. In this case, the measurement apparatus 20 provides notification that the blood fluidity is low, for example (step S206).

Subsequently, the measurement apparatus 20 confirms with the user whether to infer the state of glucose metabolism and lipid metabolism (step S207). When it is confirmed in step S207 that the state of glucose metabolism and lipid metabolism is not to be inferred (NO), the measurement apparatus 20 terminates the process. When it is confirmed in step S207 that the state of glucose metabolism and lipid metabolism is to be inferred (YES), the measurement apparatus 20 confirms whether the calculated AI was acquired before a meal or after a meal (step S208). When acquisition was not after a meal, i.e. was before a meal (NO), the process returns to step S202, and the next pulse wave is acquired. When acquisition was after a meal (YES), the measurement apparatus 20 stores the acquisition time of the pulse wave corresponding to the calculated AI (step S209). When acquisition of pulse waves is to continue (NO in step S210), the process returns to step S202, and the measurement apparatus 20 acquires the next pulse wave. When pulse wave measurement is to end (YES in step S210), the process proceeds to step S211 and beyond, and the measurement apparatus 20 infers the user's state of glucose metabolism and lipid metabolism.

Subsequently, the measurement apparatus 20 extracts the local minimums and the times thereof from a plurality of AI values calculated in step S204 (step S211). For example, in the case of the AI values illustrated by the solid curve in FIG. 15 being calculated, the measurement apparatus 20 extracts the first local minimum $AI_{P1}$ occurring 30 minutes after the meal and the second local minimum $AI_{P2}$ occurring approximately two hours after the meal.

Subsequently, the measurement apparatus 20 infers the user's state of glucose metabolism from the first local minimum $AI_{P1}$ and the time thereof (step S212). Furthermore, the measurement apparatus 20 infers the user's state of lipid metabolism from the second local minimum $AI_{P2}$ and the time thereof (step S213). Examples of inferring the user's state of glucose metabolism and lipid metabolism follow the examples described above in relationship to FIG. 15 and are therefore omitted.

Subsequently, the measurement apparatus 20 provides notification of the inference result from step S212 and step S213 (step S214) and terminates the process illustrated in FIG. 16. For example, the audio output interface 25 provides notification such as "normal glucose metabolism", "suspected abnormal glucose metabolism", "normal lipid metabolism", or "suspected abnormal lipid metabolism". The audio output interface 25 can also provide advice such as "seek advice from a doctor" or "improve your eating habits". The measurement apparatus 20 then terminates the process illustrated in FIG. 16.

In this way, the measurement apparatus 20 may include the audio output interface 25 that outputs sound. Instead of, or in addition to, an audio notification outputted from the above-described audio output interface 25, a notification may be displayed on the display 24. In this way, the measurement apparatus 20 may include the display 24 that displays information related to the measurement process performed by the controller 21. The audio output interface 25 may output sound indicating that the gyro sensor 23 is detecting the motion factor. In this way, the user can easily and reliably learn that the gyro sensor 23 in the measurement apparatus 20 is accurately detecting the motion factor.

Figure 17:
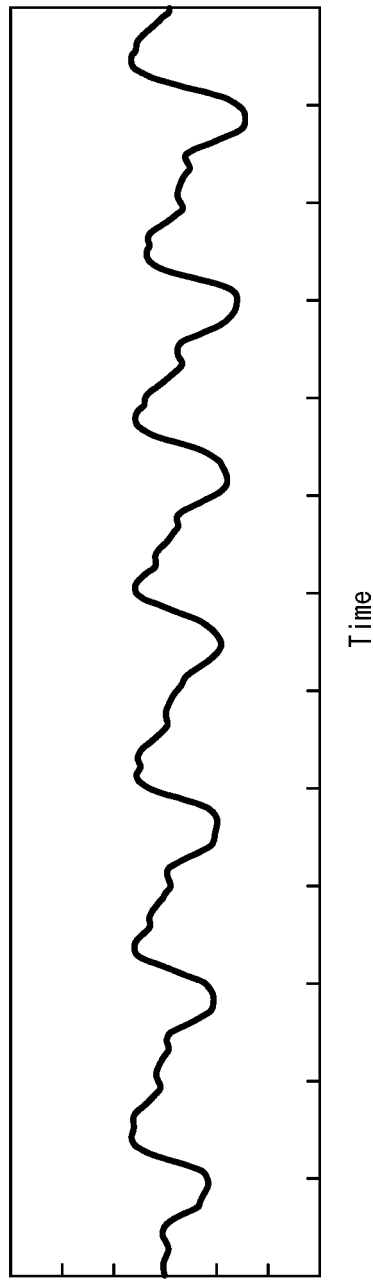
FIG. 17 illustrates an example of a respiratory waveform acquired by a sensor.

The measurement apparatus 20 can also measure the respiratory status of the user as the biological information. FIG. 17 illustrates an example of a respiratory waveform acquired by a sensor. As illustrated in FIG. 17, the respiratory waveform moves up and down cyclically in conjunction with the user's respiration. The measurement apparatus 20 can measure the user's respiratory rate per unit time, for example, based on the respiratory waveform.

Figure 18:
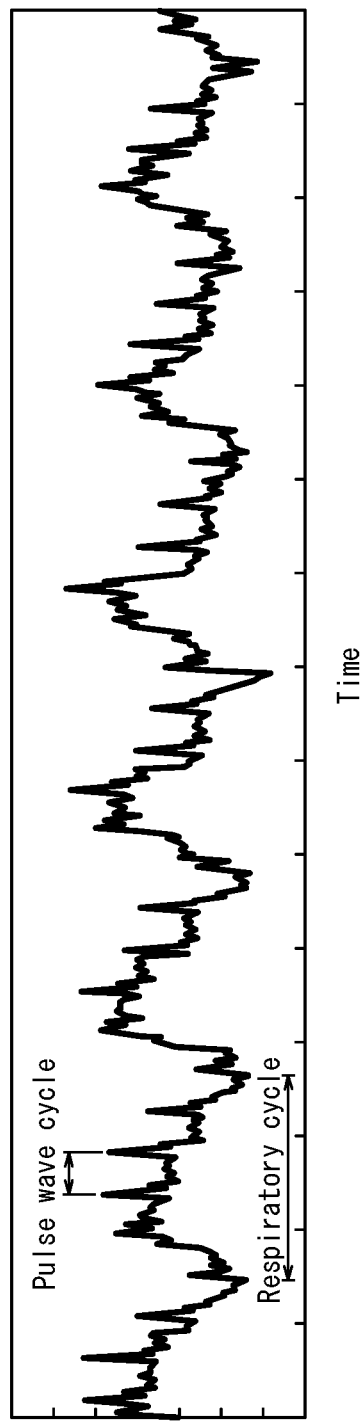
FIG. 18 illustrates an example waveform combining the pulse wave and respiration acquired by a sensor.

FIG. 18 illustrates an example waveform combining the pulse wave and respiration acquired by a sensor. For example, when abutting against the abdomen as the measured part, the measurement apparatus 20 can acquire a waveform combining the pulse wave and respiration as in the example in FIG. 18. The measurement apparatus 20 can extract the pulse wave cycle and respiratory cycle from the acquired waveform based on the interval between peaks, for example, and can calculate biological information such as the pulse wave and respiratory rate from the extracted pulse wave cycle and respiratory cycle.

As described above, the biological information measured by the measurement apparatus 20 may include information related to at least one of the user's pulse wave, pulse beat, respiration, pulse, pulse wave propagation rate, and blood flow.

Based on the biological information measured by the measurement apparatus 20, the controller 21 may infer information related to at least one of the user's physical condition, drowsiness, sleep, alertness, psychological state, body condition, feelings, psychosomatic state, mental state, autonomic nerves, stress, consciousness, blood components, sleep state, respiratory state, and blood pressure. Here, the user's "body condition" can, for example, be the presence or absence of symptoms of heat stroke, fatigue, altitude sickness, diabetes, or metabolic syndrome; the degree of such symptoms; and the presence or absence of warning signs of such symptoms. The blood components can be neutral lipids, the blood glucose level, or the like.

In this way, the holding instrument 10 according to the present embodiment allows the user to measure biological information easily with the measurement apparatus 20 by inserting the measurement apparatus 20 in the holding portion 13 and embracing the holding instrument 10. For example, when the holding instrument 10 is configured as a body pillow, the user can easily measure the biological information with the measurement apparatus 20 by embracing the holding instrument 10 when going to bed.

The holding instrument 10 has been described as a body pillow in the above embodiment. The holding instrument 10 need not, however, be configured as a body pillow. The holding instrument 10 may, for example, be configured as a stuffed animal, a doll, or the like. In this case, the stuffed animal or doll includes the holding portion 13. The holding instrument 10 can also be configured as any instrument that the user can embrace.

Figure 19:
FIG. 19 illustrates another example mode of use of a holding instrument.

In the above embodiment, the measured part has been described as the torso, but the measured part is not limited to the torso. For example, the measured part may be the user's neck. FIG. 19 illustrates an example mode of use of the holding instrument 10 when the measured part is the neck.

When the measured part is the neck, a portion of the main body 11 touches the neck when the user is embracing the holding instrument 10. The holding instrument 10 includes the holding portion 13 in the main body 11 at a position that touches the user's neck when the user is embracing the holding instrument 10. The measurement apparatus 20 held in the holding portion 13 is pressed against the user's neck and measures the biological information at the carotid artery.

The measured part is not limited to the above-described torso or neck and may be any position at which the measurement apparatus 20 can measure biological information.

When the measured part is the neck, the measurement apparatus 20 may measure the biological information while held in a holding portion 13 provided in a neck pillow, for example. In this case, the measurement apparatus 20 can measure the biological information while the user is wearing the neck pillow in a car, on a train or a plane, or the like.

When the holding instrument 10 is configured as a body pillow, for example, it is assumed that the user will often use the holding instrument 10 when going to bed. When biological information is measured while the user holds the holding instrument 10 when going to bed, the user can fall asleep more easily if the measurement apparatus 20 has a function to induce sleep. The measurement apparatus 20 may therefore have a sleep-inducing function.

Details on the sleep-inducing function are now provided. People have a respiratory rhythm that facilitates sleep. When people breathe with a rhythm that facilitates sleep, the parasympathetic nerves are stimulated, and the body relaxes. In general, the respiratory rhythm that facilitates sleep has a longer cycle than the respiratory rhythm in the waking state. The sleep-inducing function in the measurement apparatus 20 according to the present embodiment induces a rhythm that facilitates sleep into the user's respiratory cycle.

Figure 20:
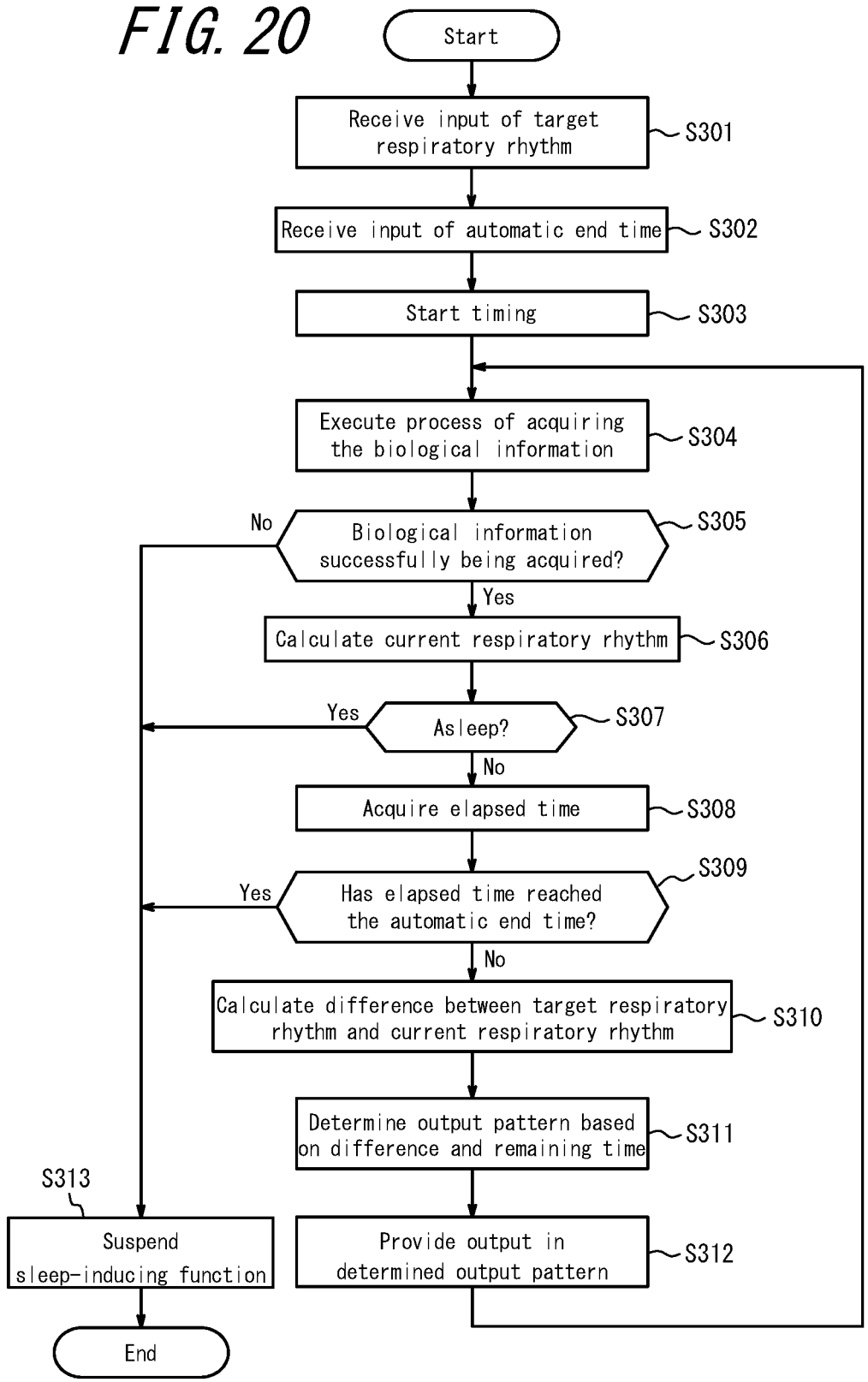
FIG. 20 is a flowchart illustrating the procedure for inducing sleep with the measurement apparatus.

FIG. 20 is a flowchart illustrating the procedure for inducing sleep with the measurement apparatus 20. The controller 21 of the measurement apparatus 20, for example, executes the process in FIG. 20.

To cause the measurement apparatus 20 to execute the sleep-inducing function, the user performs predetermined operation input to activate the sleep-inducing function. The sleep-inducing function may be executed independently or executed in parallel with the above-described process to measure biological information.

The user inputs a target respiratory rhythm into the measurement apparatus 20 in which the sleep-inducing function was activated. The measurement apparatus 20 receives input of the target respiratory rhythm (step S301). The target respiratory rhythm is the respiratory rhythm to be induced by the sleep-inducing function. The target respiratory rhythm can, for example, be inputted as a target respiratory cycle. The target respiratory rhythm may, for example, be set automatically by the measurement apparatus 20. In this case, the user need not input the target respiratory rhythm.

The user inputs an automatic end time to the measurement apparatus 20 in which the sleep-inducing function was activated. The measurement apparatus 20 receives input of the automatic end time (step S302). The automatic end time functions as a timer for the sleep-inducing function. The measurement apparatus 20 may automatically set the automatic end time. In this case, the user need not input the automatic end time.

The user inserts the measurement apparatus 20 in which the sleep-inducing function has been activated in the holding portion 13 of the holding instrument 10, for example, and embraces the holding instrument 10. The sleep-inducing function starts in this way.

The measurement apparatus 20 starts timing when execution of the sleep-inducing function starts (step S303).

The measurement apparatus 20 executes the process of acquiring the biological information (step S304). The biological information may be acquired by the measurement apparatus 20 in the same way as described in the above embodiment. As part of the sleep-inducing function, the measurement apparatus 20 may acquire respiratory information of the user as the biological information.

The measurement apparatus 20 judges whether the biological information is successfully being acquired (step S305).

When the measurement apparatus 20 judges that the biological information is not successfully being acquired (step S305: No), the measurement apparatus 20 suspends the sleep-inducing function (step S313). The measurement apparatus 20 then terminates the flow. The measurement apparatus 20 may judge that biological information is not being successfully acquired when, for example, the gyro sensor 23 is not detecting the motion factor, or when the motion factor detected by the gyro sensor 23 can be judged not to be due to biological information. It is envisioned that the measurement apparatus 20 is not properly abutted against the user, for example, when biological information is not successfully acquired. The measurement apparatus 20 therefore suspends the sleep-inducing function. For example, the measurement apparatus 20 can suspend the sleep-inducing function when the user has fallen asleep and is no longer embracing the holding instrument 10.

When suspending the sleep-inducing function, the measurement apparatus 20 may also suspend the process to measure the biological information. The measurement apparatus 20 can thereby automatically suspend the process to measure the biological information when, for example, the user is no longer embracing the holding instrument 10. When suspending the sleep-inducing function, the measurement apparatus 20 may turn the power source of the measurement apparatus 20 off. Power consumption by the measurement apparatus 20 can thereby be reduced.

When the measurement apparatus 20 judges that the biological information is successfully being acquired (step S305: Yes), the measurement apparatus 20 calculates the user's current respiratory rhythm (for example, the cycle) based on the acquired biological information (step S306).

The measurement apparatus 20 judges whether the user has fallen asleep (step S307). The measurement apparatus 20 can judge whether the user has fallen asleep based on the current respiratory rhythm calculated in step S306, for example. The user's respiratory cycle is longer than a predetermined cycle, for example, the measurement apparatus 20 can judge that the user has fallen asleep. The measurement apparatus 20 may judge whether the user has fallen asleep based on other biological information. The measurement apparatus 20 can judge whether the user has fallen asleep based on the user's pulse rate, for example. A person's pulse rate lowers when the parasympathetic nerves are stimulated and the body relaxes. Accordingly, the measurement apparatus 20 can judge that the user has fallen asleep when the user's pulse rate is less than a predetermined pulse rate.

When the measurement apparatus 20 judges that the user has fallen asleep (step S307: Yes), the measurement apparatus 20 suspends the sleep-inducing function (step S313). The measurement apparatus 20 then terminates the flow. The measurement apparatus 20 may continue measuring the biological information when judging that the user has fallen asleep.

When the measurement apparatus 20 judges that the user has not fallen asleep (step S307: No), the measurement apparatus 20 acquires the elapsed time since timing began in step S303 (step S308).

The measurement apparatus 20 judges whether the elapsed time acquired in step S308 has reached the set automatic end time (step S309).

When the measurement apparatus 20 judges that the elapsed time has reached the automatic end time (step S309: Yes), the measurement apparatus 20 suspends the sleep-inducing function (step S313). The measurement apparatus 20 then terminates the flow.

When the measurement apparatus 20 judges that the elapsed time has not reached the automatic end time (step S309: No), the measurement apparatus 20 calculates the difference between the target respiratory rhythm that was set and the current respiratory rhythm calculated in step S306 (step S310).

The measurement apparatus 20 determines the output pattern of output to provide to the user based on the difference calculated in step S311 and the remaining time until the automatic end time is reached (step S311).

The measurement apparatus 20 provides output in the determined output pattern (step S312). The output may be provided by any method recognizable by the user, including sound, vibration, or the like. The measurement apparatus 20 then proceeds to step S304.

Figure 21A:
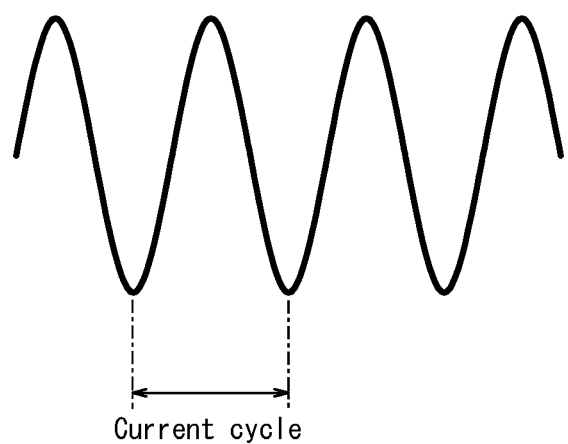
FIGS. 21A and 21B schematically illustrate examples of respiratory rhythm.
Figure 21B:
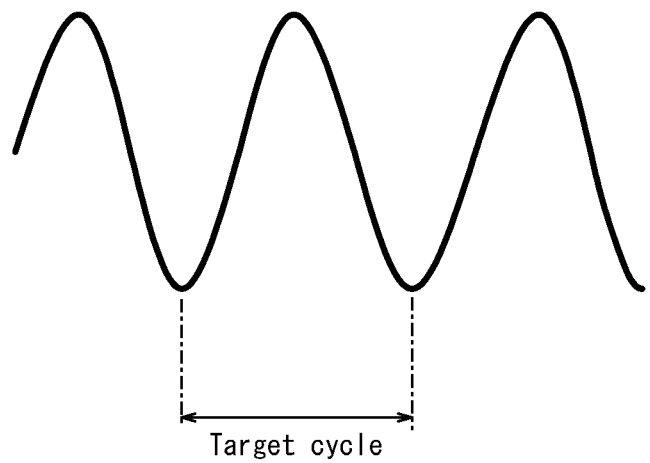

Details on step S310 to step S312 are described with reference to FIGS. 21A and 21B. FIGS. 21A and 21B schematically illustrate examples of respiratory rhythm. FIG. 21A illustrates the user's current respiratory cycle, and FIG. 21B illustrates the target respiratory cycle. When the current respiratory cycle is shorter than the target respiratory cycle, as illustrated in FIGS. 21A and 21B, the measurement apparatus 20 calculates the difference between the cycles in step S310. Then, in step S311, the measurement apparatus 20 determines the cycle of output to provide to the user based on the calculated difference and the remaining time. The cycle of output is a virtual respiratory cycle to provide to the user. For example, at the current time, the measurement apparatus 20 outputs a cycle that is the same as the user's current respiratory cycle, as illustrated in FIG. 21A. The measurement apparatus 20 determines the output pattern (cycle) so that the cycle of output gradually lengthens over time to become the target cycle illustrated in FIG. 21B by the automatic end time. The measurement apparatus 20 provides output in the determined output pattern in step S312. In other words, the output from the measurement apparatus 20 gradually lengthens over time. The output is, for example, provided by sound, vibration, or the like. The user breathes together with the outputted sound or vibration. By breathing together with changes in the output pattern from the measurement apparatus 20, the user can gradually bring the respiratory cycle closer to the target cycle. The user's respiratory cycle thereby approaches a cycle that facilitates sleep. In this way, the measurement apparatus 20 can induce sleep.

In the above embodiment, the measurement apparatus 20 has been described as being held in the holding portion 13 of the holding instrument 10 embraced by the user. However, the measurement apparatus 20 does not necessarily need to be held in a holding instrument 10 embraced by the user.

The measurement apparatus 20 can be held in any holding instrument 10 capable of maintaining the state in which the abutting portion 40 of the measurement apparatus 20 is abutted against the measured part.

Figure 22A:
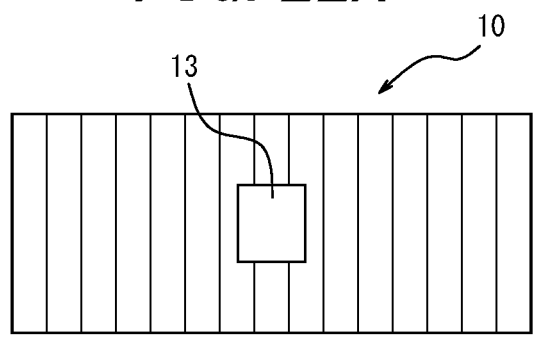
FIGS. 22A and 22B illustrate a modification to the holding instrument.
Figure 22B:
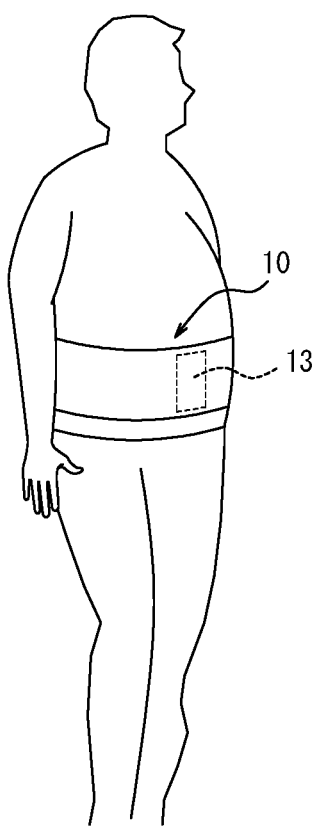

FIGS. 22A, 22B, 23A, and 23B illustrate modifications to the holding instrument 10. FIGS. 22A and 22B illustrate an example of the holding instrument 10 being configured as a belly band. The holding instrument 10 configured as a belly band includes the holding portion 13 at a position that abuts against the torso (i.e. on the inside) when the belly band is worn, as illustrated in FIG. 22A. The user can measure the biological information with the measurement apparatus 20 by inserting the measurement apparatus 20 in the holding portion 13 and wearing the belly band as illustrated in FIG. 22B.

Figure 23A:
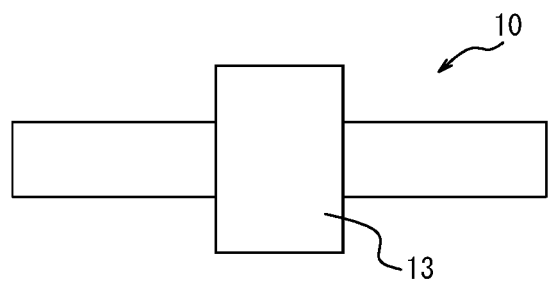
FIGS. 23A and 23B illustrate another modification to the holding instrument.
Figure 23B:
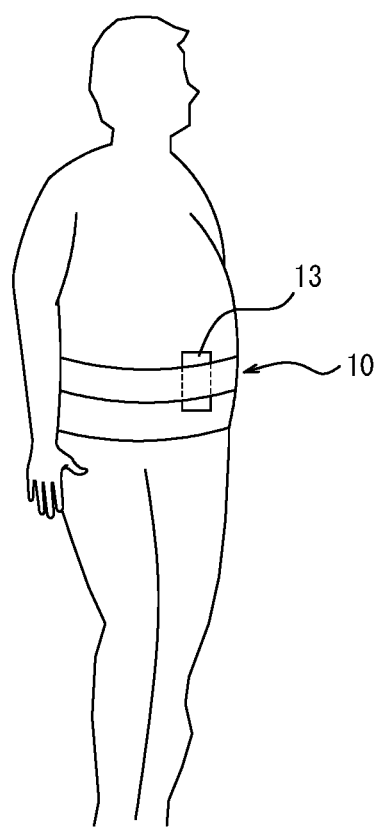

FIGS. 23A and 23B illustrate an example of the holding instrument 10 being configured as a waist belt. The holding instrument 10 configured as a waist belt includes a holding portion 13 that functions as a carrying case, as illustrated in FIG. 23A. The user can measure the biological information with the measurement apparatus 20 by inserting the measurement apparatus 20 configured as a mobile communication terminal in the holding portion 13 and wearing the waist belt as illustrated in FIG. 23B.

In the above embodiment, the holding instrument 10 configured as a body pillow has been described as including the holding portion 13 for holding the measurement apparatus 20. Instead of including the holding portion 13, however, the holding instrument 10 may include the measurement mechanism of the measurement apparatus 20 at the position of the holding portion 13. In other words, the holding instrument 10 itself may be configured as a measurement apparatus. In this case, the measurement apparatus includes functional components corresponding to the controller 21 and the gyro sensor 23 in the housing. The user can measure the biological information with the measurement apparatus while embracing the measurement apparatus, which is configured as a body pillow.

The measurement apparatus 20 may have modes of use other than those described in the above embodiments.

Figure 24:
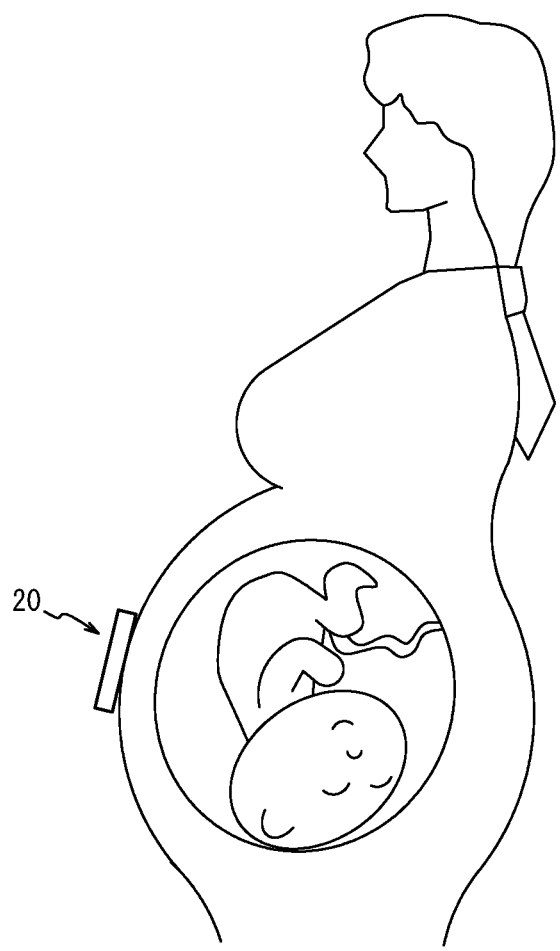
FIG. 24 illustrates another example mode of use of the measurement apparatus.

FIG. 24 illustrates another mode of use of the measurement apparatus 20. FIG. 24 schematically illustrates a pregnant mother and the unborn child in her womb. In the above embodiments, the measurement apparatus 20 has been assumed to measure the biological information of the user. However, the measurement apparatus 20 is not limited to this use.

When the user, i.e. the mother, embraces the holding instrument 10 while the measurement apparatus 20 is held in the holding portion 13 and presses the measurement apparatus 20 against the abdomen, the measurement apparatus 20 can measure the biological information of both the mother and the fetus. The holding instrument 10 is omitted from FIG. 24, which schematically illustrates the measurement apparatus 20 being pressed against the abdomen. In general, the fetus is extremely small during the first trimester of pregnancy (for example, approximately weeks 4 to 11 of pregnancy), and it is extremely difficult to hear the heartbeat directly. Accordingly, echo or the like is often used to confirm a fetal heartbeat at this stage. With use of the gyro sensor 23, however, the measurement apparatus 20 can measure biological information of the fetus, such as by detecting the fetal heartbeat.

In the mode of use illustrated in FIG. 24, the measurement apparatus 20 can measure both biological information of the fetus and biological information of the mother. The biological information of the fetus alone may therefore be extracted from the biological information measured by the measurement apparatus 20 and used. The biological information measured by the measurement apparatus 20 may thus be the biological information of the user's unborn child.

Figure 25:
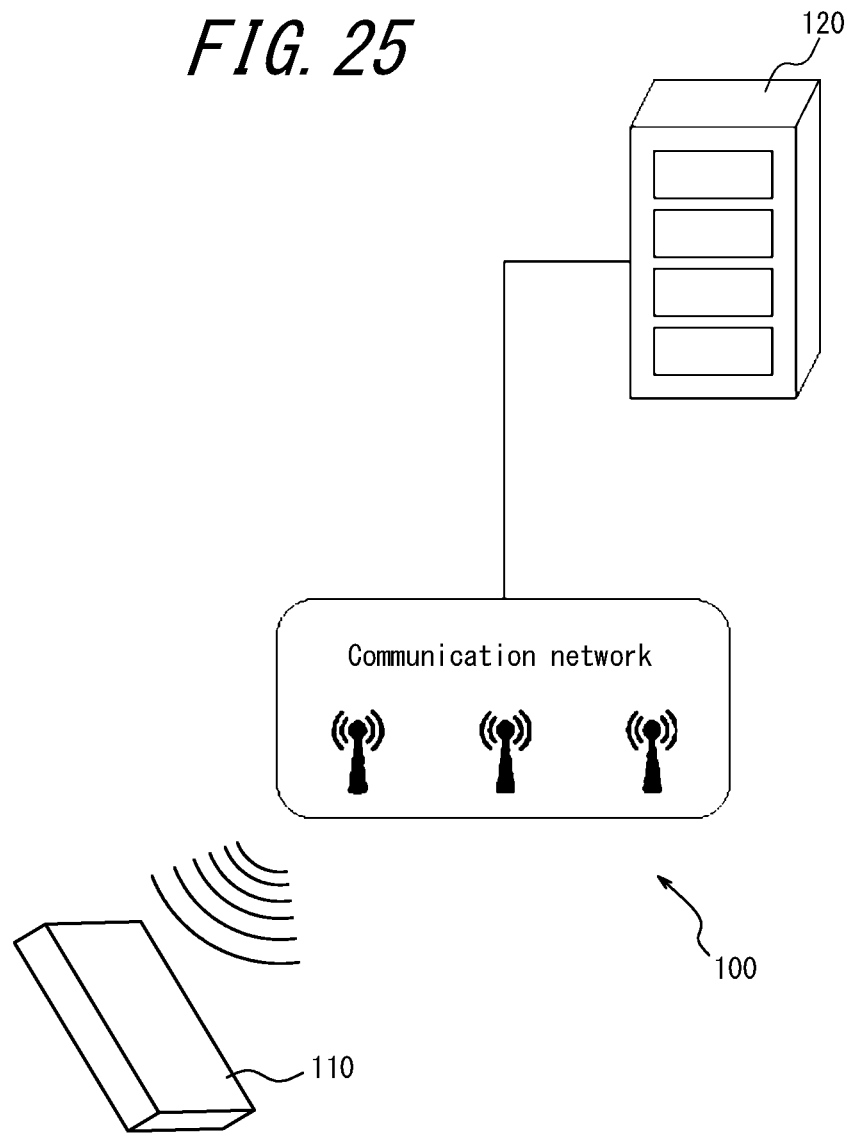
FIG. 25 schematically illustrates the configuration of a biological information measurement system according to an embodiment.

FIG. 25 schematically illustrates the configuration of a biological information measurement system 100 that uses a measurement apparatus. The biological information measurement system 100 according to an embodiment illustrated in FIG. 25 includes a measurement apparatus 110, an external apparatus 120, and a communication network.

The measurement apparatus 110 in the biological information measurement system 100 detects a motion factor due to change in the user's torso. For this purpose, the measurement apparatus 110 includes the gyro sensor 23. The measurement apparatus 110 can be configured in a similar way to the above-described measurement apparatus 20. The measurement apparatus 110 includes a communication interface (capable of wired or wireless connection) and transmits a detected motion factor to the external apparatus 120. In the biological information measurement system 100, the external apparatus 120 performs various calculations related to measurement of biological information based on the received motion factor. The external apparatus 120 therefore includes various functional components as necessary, such as the controller 21. The measurement apparatus 110 and the external apparatus 120 are assumed to be connected by wireless communication in FIG. 25, but the biological information measurement system 100 is not limited to this configuration. For example, the measurement apparatus 110 and the external apparatus 120 may be connected in a wired manner by a predetermined cable or the like.

In this way, the biological information measurement system 100 includes the measurement apparatus 110 and the external apparatus 120. The measurement apparatus 110 includes the gyro sensor 23. Here, the gyro sensor 23 detects the motion factor due to change in the user's torso while the measurement apparatus 110 is pressed against the user's torso. The external apparatus 120 includes the controller 21. The external apparatus 120 may include an artificial intelligence function, a machine learning function, a deep learning function, or the like. Based on the motion factor received from the measurement apparatus 110, the external apparatus 120 may perform various calculations related to measurement of biological information with a statistically derived algorithm.

Embodiments have been described for a complete and clear disclosure. The appended claims, however, are not limited to the above embodiments and are to be construed as encompassing all of the possible modifications and alternate configurations that a person of ordinary skill in the art could make within the scope of the fundamental features illustrated in the present disclosure. The subject matter of the various embodiments may also be freely combined.

For example, the holding instrument 10 described in the present disclosure includes the holding portion 13 in which the measurement apparatus 20 can be held. The present disclosure may, however, be embodied as a biological information measurement method using the holding instrument 10 that includes the holding portion 13 in which the measurement apparatus 20 can be held. In this case, the method includes using the gyro sensor 23 to detect the motion factor due to change in the user's torso while the measurement apparatus 20 is pressed against the user's torso. The gyro sensor 23 detects a motion factor processed as a self-control factor. The method includes performing a process to measure biological information of the user based on the motion factor detected in such a state.

The measurement apparatus 20 has been described as including the abutting portion 40 and the support 50 in the above embodiment, but the measurement apparatus 20 need not include the support 50. In this case, the abutting state of the abutting portion 40 against the measured part is supported by a portion of the back surface of the housing 31 of the measurement apparatus 20 abutting against the user at a different position than the measured part.

The abutting portion 40 has been described as being fixed to the measurement apparatus 20 in the above embodiment, but the abutting portion 40 is not necessarily fixed directly to the measurement apparatus 20. The abutting portion 40 may be fixed to a connector that is used by being fixed to the measurement apparatus 20.

The invention claimed is:

1. A holding instrument comprising:
a main body; and
a pocket attached to the main body via a ratchet configured to adjust an angle of the pocket relative to the main body, the pocket being configured to hold a measurement apparatus, the measurement apparatus comprising a gyro sensor configured to detect change in a measured part of a user and a controller configured to perform a process of measuring biological information of the user based on output of the gyro sensor;
wherein the holding instrument is embraced by the user during use while the pocket is holding the measurement apparatus.

2. The holding instrument of claim 1, wherein the holding instrument is configured to be adaptable to a body of the user.

3. The holding instrument of claim 1, wherein the holding instrument is shaped in accordance with a body shape of the user.

4. The holding instrument of claim 1, wherein a state of attachment of the pocket to a main body of the holding instrument is adjustable.

5. The holding instrument of claim 1, comprising a plurality of pockets at different positions.

6. The holding instrument of claim 1, wherein the holding instrument is cushioned.

7. The holding instrument of claim 1, wherein the holding instrument is configured as at least one of a body pillow, a stuffed animal, and a doll.

8. The holding instrument of claim 1, wherein the measurement apparatus is pressed against the user while the holding instrument is embraced by the user.

9. The holding instrument of claim 1, wherein the measurement apparatus is pressed against a torso of the user while the holding instrument is embraced by the user.

10. The holding instrument of claim 9, wherein when the holding instrument is embraced by the user, a portion of the measurement apparatus is pressed against the torso while at least a portion other than the portion pressed against the torso is pressed against a waistband of clothing or a belt of the user, and the measurement apparatus detects the change.

11. The holding instrument of claim 9, wherein when the holding instrument is embraced by the user, a portion of the measurement apparatus is pressed against a side of the torso while at least a portion other than the portion pressed against a side of the torso is pressed towards a center of the torso from the side, and the measurement apparatus detects the change.

12. The holding instrument of claim 9, wherein when the holding instrument is embraced by the user, a portion of the measurement apparatus is pressed against a lower abdomen side of the torso while at least a portion other than the portion pressed against a lower abdomen side of the torso is pressed towards a top of the torso from the lower abdomen side, and the measurement apparatus detects the change.

13. The holding instrument of claim 1, wherein the pocket is configured so that a notification outputted by the measurement apparatus is recognizable by the user.

14. The holding instrument of claim 13, wherein the notification comprises at least one of sound, screen display, and vibration.

15. The holding instrument of claim 1, wherein the measurement apparatus is a mobile communication terminal.

16. A measurement method for a measurement apparatus comprising a gyro sensor configured to detect change in a measured part of a user, the measurement method comprising:
  performing a process of measuring biological information of the user based on output of the gyro sensor while the user is embracing a holding instrument that holds the measurement apparatus,
  wherein the holding instrument includes:
    a main body; and
    a pocket attached to the main body via a ratchet configured to adjust an angle of the pocket relative to the main body, the pocket being configured to hold the measurement apparatus.

* * * * *